(12) United States Patent
Ochiai et al.

(10) Patent No.: US 7,425,567 B2
(45) Date of Patent: Sep. 16, 2008

(54) PIPERIDINE DERIVATIVE COMPOUNDS AND DRUGS CONTAINING THE COMPOUNDS AS THE ACTIVE INGREDIENT

(75) Inventors: Hiroshi Ochiai, Mishima-gun (JP); Yoshitaka Nishita, Sakai-gun (JP); Tazumi Ohtani, Mishima-gun (JP); Masaya Hamano, Sakai-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 531 days.

(21) Appl. No.: 10/504,028

(22) PCT Filed: Feb. 7, 2003

(86) PCT No.: PCT/JP03/01318

§ 371 (c)(1), (2), (4) Date: Aug. 9, 2004

(87) PCT Pub. No.: WO03/066590

PCT Pub. Date: Aug. 14, 2003

(65) Prior Publication Data

US 2005/0080107 A1    Apr. 14, 2005

(30) Foreign Application Priority Data

Feb. 8, 2002   (JP) .............................. 2002-031602

(51) Int. Cl.
*A61K 31/445*   (2006.01)
*C07D 211/56*   (2006.01)

(52) U.S. Cl. ...................................... 514/331; 546/215

(58) Field of Classification Search .................. 546/215; 514/331
See application file for complete search history.

(56) References Cited

U.S. PATENT DOCUMENTS 7,109,342 B2 *  9/2006  Nakai et al. ................. 546/192

FOREIGN PATENT DOCUMENTS

| WO | WO 93/19747 A1 | 10/1993 |
| WO | WO 94/25437 A1 | 11/1994 |
| WO | WO 02/14280 A1 | 2/2002 |

OTHER PUBLICATIONS

Seddon "Pseudopolymorph . . . " Crystal growth and design, 496) 1087 (2004).*
Evans "An introduction to crystal chemistry" Cambridge press, p. 393-396 (1964).*
Braga et al. "Making crystals . . . " Chem. Commun. p. 3635-3645 (2005).*
Down et al. "Clinical pharmacology of . . . " Clin. Pharmcokineti. v.45(3), p. 217-233 (2006).*

* cited by examiner

*Primary Examiner*—Celia Chang
(74) *Attorney, Agent, or Firm*—Sughrue Mion, PLLC

(57) ABSTRACT

A piperidine derivative of formula (I)

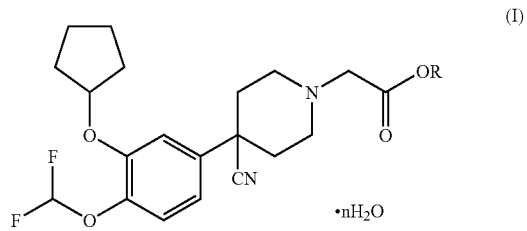

(wherein all symbols are as described in the specification.) and an intermediate for the preparation thereof. The compound of formula (I) has phosphodiesterase 4 inhibitory activity, and it is useful for the prevention and/or treatment of inflammatory diseases, diabetic diseases, allergic diseases, autoimmune diseases, ocular diseases, osteoporosis, bone fracture, osteoarthritis, obesity, bulimia, depression, Parkinson's disease, dementia, ischemia-reperfusion injury, leukemia, acquired immunodeficiency deficiency syndrome (AIDS), shock, systemically inflammatory responsive diseases (SIRS), etc.

4 Claims, 10 Drawing Sheets

PIPERIDINE DERIVATIVE COMPOUNDS AND DRUGS CONTAINING THE COMPOUNDS AS THE ACTIVE INGREDIENT

TECHNICAL FIELD

The present invention relates to a piperidine derivative.
More specifically, the present invention relates to
(1) a piperidine derivative of formula (I)

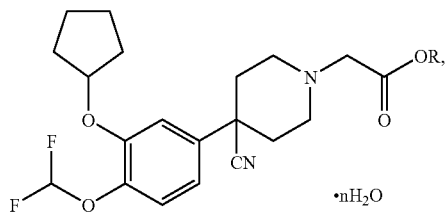

(2) a method for the preparation thereof,
(3) a composition comprising it as an active ingredient,
(4) a compound of formula (III):

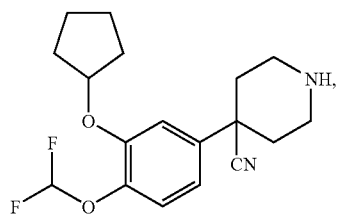

which is useful as an intermediate for the preparation of the compound of formula (I), and
(5) a method for the preparation thereof.

BACKGROUND ART

Cyclic adenosine 3',5'-monophosphate (cAMP) and cyclic guanosine 3',5'-monophosphate (cGMP) as intracellular signal transduction molecules (second messengers) are degraded by a group of hydrolases generally called phosphodiesterase (PDE) into inactive 5'-AMP and 5'-GMP, respectively.

PDE isozymes which inactivate them are not uniformly present in vivo but distributed in vivo having an organ-specific localization by showing differences, e.g., in cell distribution and tissue distribution.

Up to date, the presence of 11 families of PDE1 to PDE11 has been confirmed (see *Current Opinion in Cell Biology*, 12, 174-179 (2000)).

Among these PDEs, PDE4 is present in various cells such as airway smooth muscle cells, epitherial cells, inflammatory cells (macrophages, neutrophils and eosinophils) and T lymphocytes, etc. and controls cellular functions by regulating the intracellular cAMP level of these cells. On the other hand, other PDEs such as PDE5 etc. are present in, e.g., platelets, cardiac muscle cells and vascular smooth muscle cells and participate in the control of circulatory organ system by regulating intracellular cGMP or cAMP level.

Thus, it is known that PDE4 inhibitors have bronchodilatory activity, anti-inflammatory activity, mediator release inhibitory activity, immunosuppressive activity and the like, because they cause accumulation of intracellular cAMP by inhibiting degradation of cAMP by PDE4.

Accordingly, it is considered that agents which specifically inhibit PDE4 do not show the activities of other PDE inhibition such as PDE5 upon circulatory organs and are useful in preventing and/or treating various diseases such as inflammatory diseases (e.g. asthma, obstructive lung disease, sepsis, sarcoidosis, nephritis, hepatitis, enteritis, etc.), diabetic diseases, allergic diseases (e.g. allergic rhinitis, allergic conjunctivitis, seasonal conjunctivitis, atopic dermatitis, etc.), autoimmune diseases (e.g. ulcerative colitis, Crohn's disease, rheumatism, psoriasis, multiple sclerosis, collagen disease, etc.), ocular diseases (e.g. allergic conjunctivitis, seasonal conjunctivitis, etc.), osteoporosis, bone fracture, osteoarthritis, obesity, bulimia, depression, Parkinson's disease, dementia, ischemia-reperfusion injury, leukemia and AIDS (*Exp. Opin. Invest. Drugs*, 8, 1301-1325 (1999)), shock, systemically inflammatory responsive diseases (SIRS), etc.

As PDE4 inhibitors, for example, the specification of JP Hei 8-509731 (i.e. WO94/25437) discloses that a compound of formula (A)

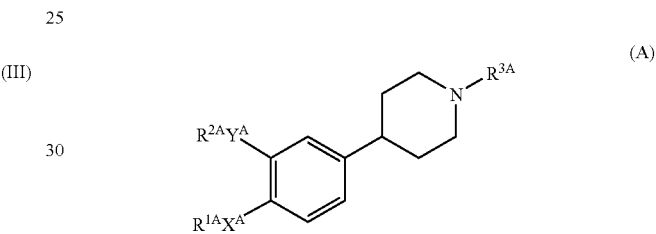

(wherein $R^{1A}$ represents H or C1-6 alkyl; $R^{2A}$ represents C3-7 alkyl, C3-7 cycloalkyl, etc.; $R^{3A}$ represents $COR^{4A}$, $COCOR^{4A}$, etc.; $R^{4A}$ represents H, $OR^{5A}$, NHOH, etc.; $R^{5A}$ represents H, C1-6 alkyl, etc.; $X^A$ represents O etc.; and $Y^A$ represents O etc.) or a pharmaceutically acceptable salt thereof has a PDE4 inhibitory activity.

Also, the specification of WO 93/19747 discloses that a compound of formula (B)

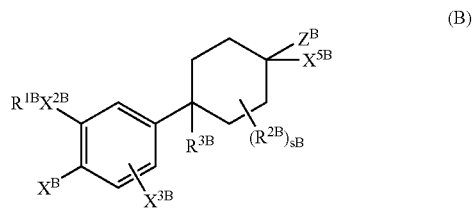

(wherein $R^{1B}$ represents $—(CR^{4B}R^{5B})_{rB}R^{6B}$ etc., rB is 1 to 6; $R^{4B}$ and $R^{5B}$ each independently represents a hydrogen atom or a C1-2 alkyl group; $R^{6B}$ represents a hydrogen atom, a C3-6 cycloalkyl group, etc.; $X^B$ represents $Y^B R^{2B}$ etc.; $Y^B$ represents O etc.; $R^{2B}$ represents methyl, ethyl, etc.; $X^{2B}$ represents O etc.; $X^{3B}$ represents a hydrogen atom etc.; sB is 0 to 4; $R^{3B}$ represents a hydrogen atom, CN, etc.; $X^{5B}$ represents a hydrogen atom etc.; $Z^B$ represents $CR^{8B}R^{8B}C(O)OR^{14B}$, $CR^{8B}R^{8B}C(Y^{B})NR^{10B}R^{14B}$, etc.; $R^{8B}$ represents a hydrogen atom etc.; $R^{10B}$ represents a hydrogen atom, $OR^{8B}$, etc.; and $R^{14B}$ represents a hydrogen atom etc.) or a pharmaceutically acceptable salt thereof has a PDE4 inhibitory activity.

Also, the specification of WO 93/19749 discloses that a compound of formula (C)

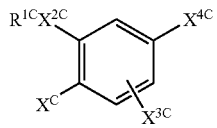

(wherein $R^{1C}$ represents —$(CR^{4C}R^{5C})_{rC}R^{6C}$, etc.; rC is 1 to 6; $R^{4C}$ and $R^{5C}$ each independently represents a hydrogen atom or a C1-2 alkyl group; $R^{6C}$ represents a hydrogen atom, a C3-6 cycloalkyl group, etc.; $X^{C}$ represents $Y^{C}R^{2C}$ etc.; $Y^{C}$ represents O, etc.; $R^{2C}$ represents methyl, ethyl, etc.; $X^{2C}$ represents O, etc.; $X^{3C}$ represents a hydrogen atom etc.; $X^{4C}$ represents

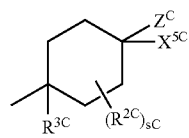

etc.; $R^{3C}$ represents a hydrogen atom, CN, etc.; $X^{5C}$ represents a hydrogen atom etc.; sC is 0 to 4; $Z^{C}$ represents C(O) $OR^{14C}$, $C(Y'^{C})NR^{10C}R^{14C}$, etc.; $R^{10C}$ represents a hydrogen atom $OR^{8C}$, etc.; $R^{8C}$ represents a hydrogen atom etc.; and $R^{14C}$ represents a hydrogen atom etc.) or a pharmaceutically acceptable salt thereof has a PDE4 inhibitory activity.

The present applicant previously filed a patent application about piperidine derivative of formula (D)

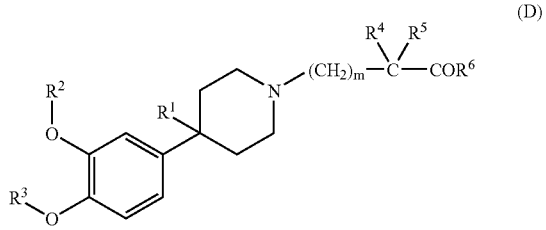

(wherein all symbols have the same meanings as described in PCT/JP01/06861.) and a non-toxic salt thereof and a PDE4 inhibitor comprising it as an active ingredient (see the specification of WO 02/14280). Particularly, example 2(9) in the world patent application discloses 2-(4-(3-cyclopentyloxy-4-difluoromethoxyphenyl)-4-cyanopyperidin-1-yl acetic acid of formula (E)

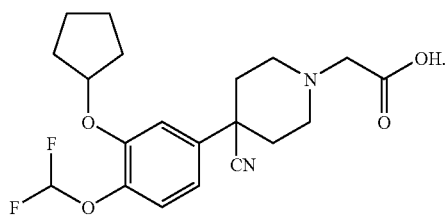

DISCLOSURE OF THE INVENTION

In order to find a compound having a PDE4 inhibitory activity, the present inventors have conducted intensive studies and found, as a result, that the objects can be accomplished by the piperidine derivative of formula (I), and thus the present invention has been accomplished.

The compound of formula (I), especially 2-(4-(3-cyclopentyloxy-4-difluoromethoxyphenyl)-4-cyanopiperidin-1-yl)acetic acid, monohydrate (abbreviated as compound 1 hereafter.) is not described in the above world application concretely, and it is an utterly novel compound.

Also, the present inventors have found a compound of formula (III), which is very useful as an intermediate for the preparation of piperidine derivative of formula (III), and the present invention has been accomplished.

The present invention relates to
(1) 2-(4-(3-cyclopentylpxy-4-difluoromethoxyphenyl)-4-cyanopiperidin-1-yl) acetic acid monohydrate of formula (I):

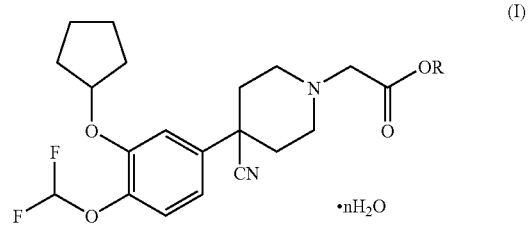

wherein R is hydrogen, alkali metal atom, alkaline earth metal or organic amine, n is an integer of 1 to 5, or proper fraction or improper fraction up to 5,
(2) the piperidine derivative according to the above (1), wherein R is hydrogen,
(3) the piperidine derivative according to the above (1), wherein n is 1,
(4) the compound according to any one of the above (1) to (3), which is 2-(4-(3-cyclopentyloxy-4-difluoromethoxyphenyl)-4-cyanopiperidin-1-yl)acetic acid monohydrate,
(5) 4-(3-cyclopentyloxy-4-difluoromethoxyphenyl)-4-cyanopiperidine of formula (III) or an acid-addition salt thereof:

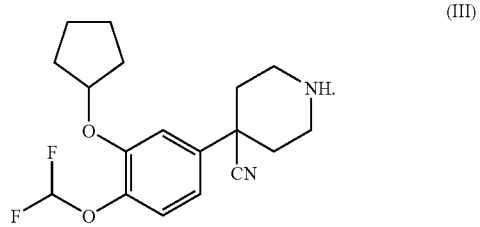

(6) a method for the preparation of 2-(4-(3-cyclopentyloxy-4-difluoromethoxyphenyl)-4-cyanopiperidin-1-yl)acetic acid.$nH_2O$, wherein n has the same meaning as in the above (1), which comprises carrying out recrystallization in an alcohol solvent optionally mixed with water and/or one or more organic solvent,
(7) a PDE4 inhibitor comprising the compound according to any one of the above (1) to (4) as an active ingredient,
(8) a composition for the prevention and/or treatment of inflammatory diseases, diabetic diseases, allergic diseases, autoimmune diseases, ocular diseases, osteoporosis, bone fracture, osteoarthritis, obesity, bulimia, depression, Parkinson's disease, dementia, ischemia-reperfusion injury, leukemia, AIDS, shock, systemically inflammatory responsive diseases (SIRS), which comprises the compound according to any one of the above (1) to (4) as an active ingredient, (9) the composition for the prevention and/or treatment according to the above (8), wherein the inflammatory disease is asthma, chronic obstacle pulmonary disease, sepsis, sarcoidosis, nephritis, hepatitis or enteritis,

(10) the composition for the prevention and/or treatment according to the above (8), wherein the allergic disease is allergic rhinitis or atopic dermatitis,

(11) the composition for the prevention and/or treatment according to the above (8), wherein the autoimmune disease is ulcerative colitis, Crohn's disease, rheumatism, psoriasis, multiple sclerosis or collagen disease,

(12) the composition for the prevention and/or treatment according to the above (8), wherein ocular disease is allergic conjunctivitis or seasonal conjunctivitis and

(13) a method for the preparation of the compound of formula (III) according to the above (5).

In the present specification, an integer of 1 to 5 which n represents, is 1, 2, 3, 4 and 5.

In the present specification, proper fraction from 1 to 5 which n represents is, for example, ½, ⅓, ¼, etc., and improper fraction is, for example, 3/2, 10/2, etc.

In the present specification, metals which R represents include all pharmaceutically acceptable ones, for example, alkali metals, alkaline earth metals, etc. Alkali metals include potassium, sodium, lithium, etc., alkaline earth metals include calcium, magnesium, etc.

In the present specification, organic amines which R represents include whichever forms a salt and is pharmaceutically acceptable, for example, triethylamine, methylamine, dimethylamine, cyclopentylamine, benzylamine, phenethylamine, piperidine, monoethanolamine, diethanolamine, tris(hydroxymethyl)methylamine, lysine, arguinine, N-methyl-D-glucamine, etc.

$nH_2O$ in formula (I) is, crystallization water and adhesion water, Crystallization water is preferable as $nH_2O$.

In the compound of formula (I), when subjected to pharmaceuticals, R is preferably hydrogen and n is preferably 1.

METHODS FOR THE PREPARATION OF THE COMPOUND OF THE PRESENT INVENTION

Figure 1:
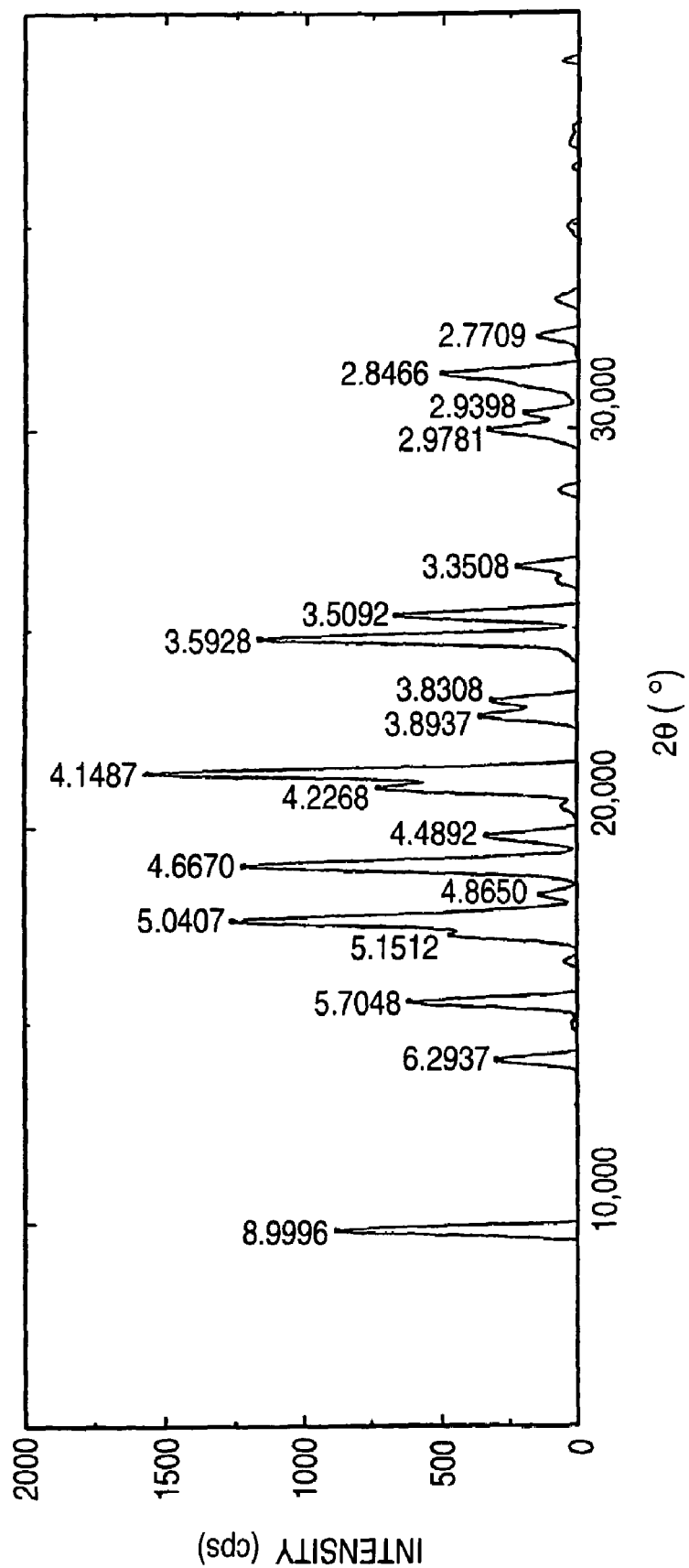
FIG. 1 shows a powder X-ray diffraction spectrum of 2-(4-(3-cyclopentyloxy-4-difluoromethoxyphenyl)-4-cyanopiperidin-1-yl)acetic acid monohydrate (compound 1).

The compounds of the present invention of formula (I) and (III) may be prepared according to the following methods or methods described in the examples.

The compound of the present invention of formula (I) may be prepared by subjecting to a deprotection reaction of protective groups of carboxy the compound of formula (II)

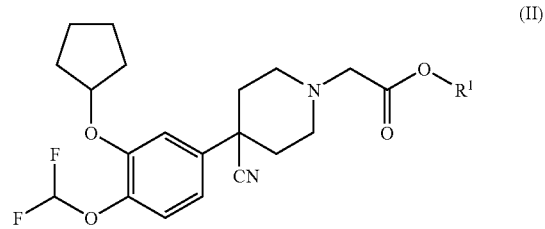

(II)

(wherein $R^1$ is a protective group of carboxy.).

Protective groups for carboxy include, for example, methyl, ethyl, t-butyl, benzyl, etc.

Protective groups for carboxy are not limited to above listed, but other groups may also be used instead, if easily and selectively eliminated. For example, the groups described in T. W. Greene, Protective Groups in Organic Synthesis 3rd edition, Wiley, New York, 1999 may be used.

The deprotection reaction of protecting groups of a carboxy is known, and examples include (1) a deprotection reaction under alkaline conditions,
(2) a deprotection reaction under acidic conditions,
(3) a deprotection reaction by hydration, etc.

These methods are specifically described below.

(1) The deprotection reaction under alkaline conditions is carried out, for example, in an organic solvent (e.g., methanol, tetrahydrofuran, dioxane, dimethylformamide, etc.) using an alkali metal hydroxide (e.g., sodium hydroxide, potassium hydroxide, lithium hydroxide, etc.), an alkaline earth metal hydroxide (e.g., barium hydroxide, calcium hydroxide, etc.) or a carbonate (e.g., sodium carbonate, potassium carbonate, etc.), an organic amine (e.g., triethylamine, diisopropylethylamine, piperazine, etc.) or a quaternary ammonium salt (e.g., tetrabutylammonium fluoride etc.) or an aqueous solution thereof or a mixture thereof at a temperature between 0 and 40° C.

(2) The deprotection reaction under acidic conditions is carried out, for example, in an organic solvent (e.g., methylene chloride, chloroform, dioxane, ethyl acetate, anisole, etc.) using an organic acid (e.g., acetic acid, trifluoroacetic acid, methanesulfonic acid, etc.), an inorganic acid (e.g., hydrochloric acid, sulfuric acid, etc.) or a mixture thereof (e.g., hydrogen bromide/acetic acid etc.) at a temperature between 0 and 100° C.

(3) The deprotection reaction of hydration is carried out, for example, in a solvent (e.g., ethers (tetrahydrofuran, dioxane, dimethoxyethane, diethyl ether, etc.), alcohols (methanol, ethanol, etc.), benzenes (benzene, toluene, etc.), ketones (acetone, methyl ethyl ketone, etc.), nitriles (acetonitrile, etc.), amides (dimethylformamide etc.), water, ethyl acetate, acetic acid or a mixture of two or more selected from above in the presence of a catalyst (palladium-carbon, palladium black, palladium hydroxide, platinum oxide, Raney nickel, etc.) under atmosphere of normal or increased pressure of hydrogen or in the presence of ammonium formate at a temperature between 0 and 200° C.

As easily understood by those skilled in the art, the compounds of the present invention may be easily prepared by these reactions.

Also, the compound of formula (I) may be prepared by optionally subjecting to a reaction of converting to a salt, recrystallization, or drying after deprotection reactions.

Converting to a salt, recrystallization and drying are known, for example, they may be carried out according to a method of 'The fourth series of experimental chemistry No. 1, Basic operation No. 1 (edition by The Chemical Society of Japan)'.

Solvents which are used in the recrystallization are, for example, water and/or alcohol solvents optionally comprising one organic solvent or more.

Alcohol solvents include those solvents which are alkanes possessing hydroxy in its structure, for example, methanol, ethanol, propanol, isopropanol, butanol, etc.

Organic solvents include whichever solvent that is used in recrystallization, for example; chain ether solvents, ring ether solvents, amide solvents, phosphorus amide solvents, sulfur-containing solvents, nitrile solvents, ester solvents, ketone solvents, carbonate solvents, carboxylic acid solvents, chain alkane solvents, ring alkane solvents, aromatic carbocyclic solvents, cyclic nitrogen-containing solvents.

Chain ether solvents include solvents which possess ether bond in its structure, and takes chain structure. The substituents on the carbon which constitutes ether bond may be chain or ring, for example, 1,2-dimethoxyethane, cyclopentyl methyl ether, diethyl ether, isopropyl ether, and methyl-t-butyl ether, etc.

Ring ether solvents include solvents which possess ether bond in its structure, for example, tetrahydrofuran, 1,4-dioxane, etc.

Amide solvents include solvents which possess amide bond in its structure, for example, N,N-dimethylacetamide, N,N-dimethylformamide, etc.

Phosphorus amide solvents include solvents which possess phosphorus amide structure in its structure, for example, hexamethylphosphorus triamide, etc.

Sulfur-containing solvents include solvents which possesses sulfur atom in its structure, for example, dimethylsulfoxide, tetramethylenesulfoxide, etc.

Nitrile solvents include solvents which possesses nitrile radical in its structure, for example, acetonitrile etc.

Ester solvents include solvents which possess ester bond in its structure, ethyl acetate, etc.

Ketone solvents include solvents which possess ketone radical in its structure, for example, acetone, methylketone, etc.

Carbonate solvents include solvents which possess carboxy radical in its structure, for example, acetic acid.

Chain alkane solvents include solvents whose structure is chain alkane, for example, pentane, n-hexane, heptane, etc.

Ring alkane solvents include solvents whose structure is ring alkane, for example, cyclohexane etc.

Aromatic carbocyclic solvents include solvents of aromatic carbocycles, for example, benzene, toluene, xylene, etc.

Cyclic nitrogen-containing solvents include solvents which possess nitrogen atom(s) and takes ring structure, for example, pyridine, piperidine, 1,3-dimethyl-2-imidazolidinone, 1-methyl-2-pyrrolidone, etc.

Drying operation includes, for example, natural drying, air drying, forced drying (using drying agent, drying under reduced pressure, etc.).

The compound of formula (II) may be prepared according to reaction schemes 1 and 2 hereafter described or examples.

The compound of formula (III) is novel, and it may be prepared by subjecting to deprotection reaction of the compound of formula (IV)

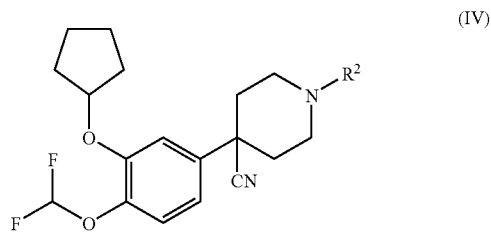

(IV)

(wherein $R^2$ is a protective group of amino).

Protective groups for amino include, for example, benzyl, 4-methoxybenzyl, benzyloxycarbonyl, t-butoxycarbonyl, trifluoroacetyl, 9-fluorenylmethoxycarbonyl, etc.

Protective groups for amino are not limited to above listed, but other groups may also be used instead, if easily and selectively eliminated. For example, the groups described in T. W. Greene, Protective Groups in Organic Synthesis 3rd edition, Wiley, New York, 1999 may be used.

Deprotection reactions of protective groups of amino is known, for example, (1) a deprotection reaction under alkaline conditions, (2) a deprotection reaction under acidic conditions, (3) a deprotection reaction by hydration, etc are known.

To describe these methods concretely, (1) A deprotection reaction under alkaline conditions is, for example, carried out in an organic solvent (methanol, ethanol, tetrahydrofuran, dioxane, dimethylformamide, etc.) using a hydroxide of alkali metals (sodium hydroxide, potassium hydroxide, lithium hydroxide, etc.), hydroxide of alkaline earth metals (barium hydroxide, calcium hydroxide, etc.), or a carbonate (sodium carbonate, potassium carbonate, etc.), an organic amine (triethylamine, diisopropylethylamine, piperazine, piperidine, morpholine, etc.) or a quaternary ammonium salt (tetrabutyl ammonium fluoride, etc.) or a solution thereof or a mixture thereof at a temperature between 0 and 40° C.

(2) A deprotection reaction under acidic conditions is, for example, carried out in or without an organic solvent (methylene chloride, chloroform, dioxane, ethyl acetate, anisole, etc.), using an organic acid (acetic acid, trifluoroacetic acid, methanesulfonic acid, etc.) or an inorganic acid (hydrochloric acid, sulfuric acid, etc.) or a mixture thereof (hydrobromic acid/acetic acid, etc.) at a temperature between 0 and 100° C.

(3) A deprotection reaction by hydration is, for example, carried out in a solvent (ethers (tetrahydrofuran, dioxane, dimethoxyethane, diethyl ether, etc.), alcohols (methanol, ethanol, etc.), benzenes (benzene, toluene, etc.), ketones (acetone, methyl ethyl ketone, etc.), nitrites (acetonitrile etc.), amides (dimethylformamide etc.), water, ethyl acetate, acetic acid or a mixture of more than two from above etc.) in the presence of a catalyst (palladium-carbon, palladium black, palladium hydroxide, platinum oxide, Raney nickel, etc.) under atmosphere of hydrogen of normal or suppressed pressure, or in the presence of ammonium formate at a temperature between 0 and 200° C.

As easily understood by those skilled in the art, the compounds of the present invention may be easily prepared by these deprotection reactions.

The compound of formula (IV) may be prepared by the method described in the following reaction scheme 3 or in the examples.

In the reaction schemes, $R^3$ is a protective group of phenol, X is a leaving group (chlorine, bromine, iodine, tosyl, mesyl, etc.) and the other symbols have the same meanings as hereinbefore.

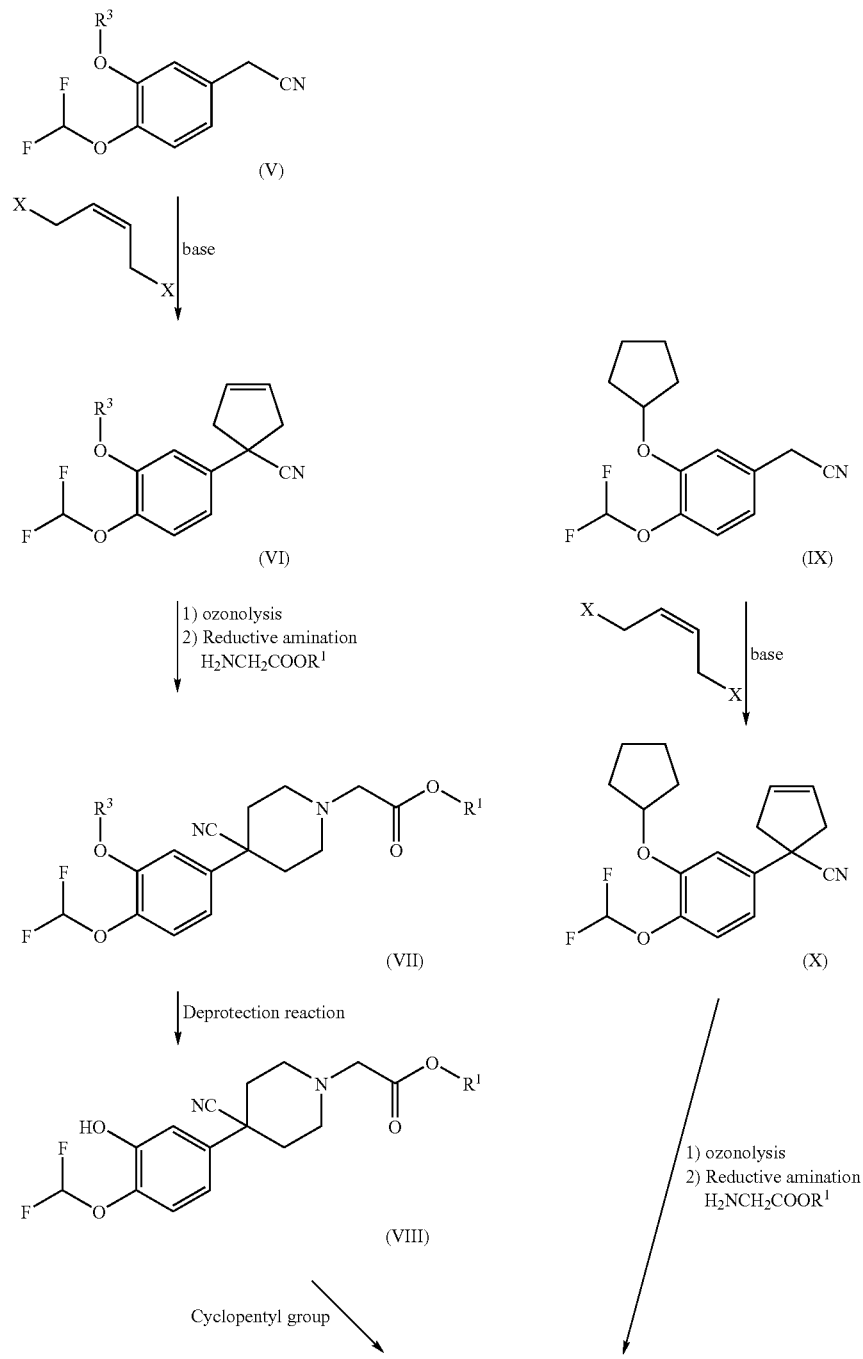

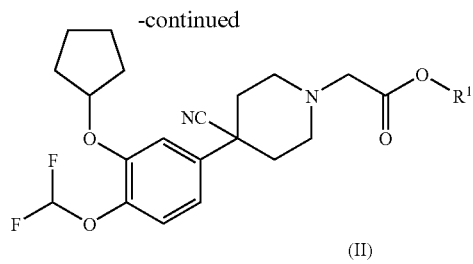
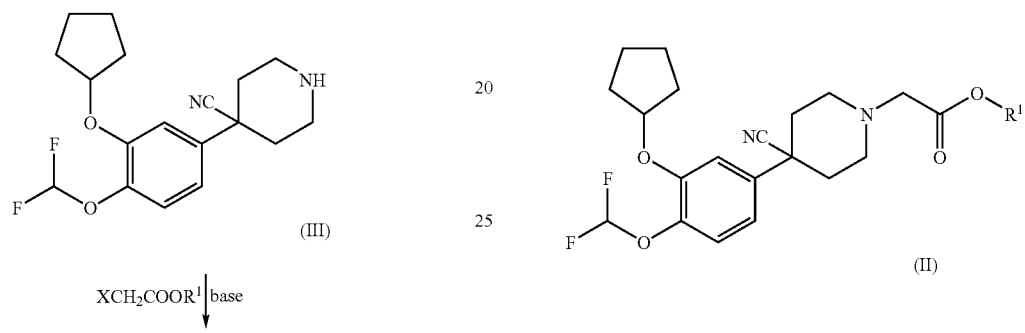
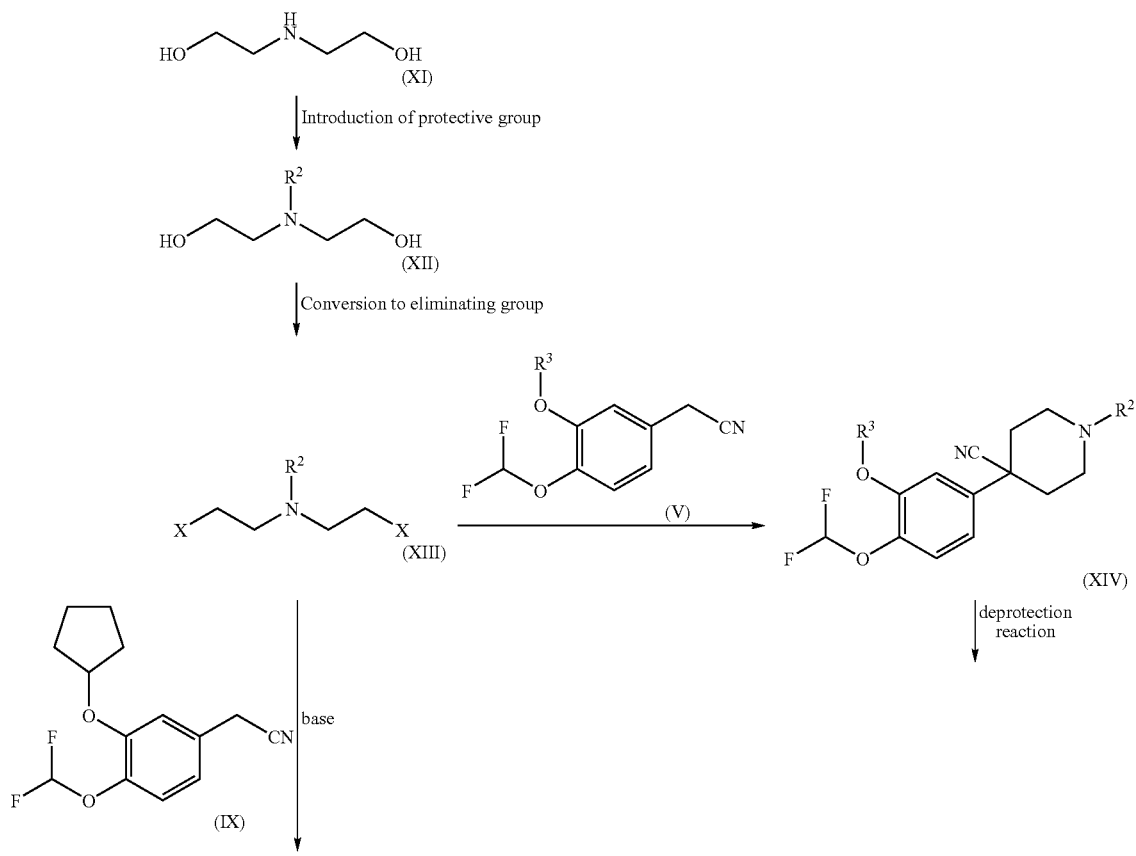

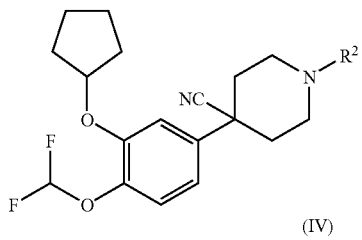

(IV)

cyclopentyl group →

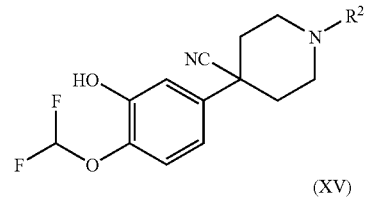

(XV)

In each reaction in the present invention, the reaction products may be purified by conventional techniques, for example, distillation under normal or reduced pressure, high performance liquid chromatography, thin layer chromatography or column chromatography using silica gel or magnesium silicate. Purification may be carried out after each reaction, or after a series of reactions.

Salt:

The compound of the present invention of formula (III) may be converted to acid-addition salt by a conventional method.

Acid-addition salts, of the compound of formula (III) include, for example, inorganic acid salts such as hydrochloride, hydrobromide, hydroiodate, sulfate, phosphate, and nitrate; and organic acid salts such as acetate, lactate, tartarate, benzoate, citrate, methane sulfonate, ethane sulfonate, benzene sulfonate, toluene sulfonate, isethionate, glucuronate, and gluconate.

The compound of the present invention of formula (I), especially monohydrate (compound 1 hereafter described) is applicable to preparing a stable formulation, particularly solid formulation (e.g. tablets, capsules, etc.). That is, the anhydrate (comparison compound hereafter described) could turn into a mixture of anhydrate and monohydride by absorbing atmospheric vapors during the preparation of solid formulation or its storage, whereas the compound of the present invention does not cause such morphological change; therefore, the compound of the present invention is very useful.

Comparison Test:

It was confirmed by the following comparison examinations (powder X-ray diffraction data, IR (infrared) data, DSC (differential scanning calorimetry) data, TG (thermogravimetry) data, elemental analysis data, monocrystal X-ray structural analysis data) that the two compounds are completely different; i.e. 2-(4-(3-cyclopentyloxy-4-difluoromethoxyphenyl)-4-cyanopiperidin-1-yl)acetic acid monohydrate (compound 1; this compound was prepared by the method of example 2 hereafter described) among the compound of the present invention of formula (I) and 2-(4-(3-cyclopentyloxy-4-difluoromethoxyphenyl)-4-cyanopiperidin-1-yl)acetic acid (abbreviated as comparison compound) of comparison example 1 as described hereafter, according to example 2(9) of world patent application No. PCT/JP00/06861 (i.e. WO02/14280), which is described in the above world patent application.

1) Powder X-ray Diffraction Data

Figure 2:
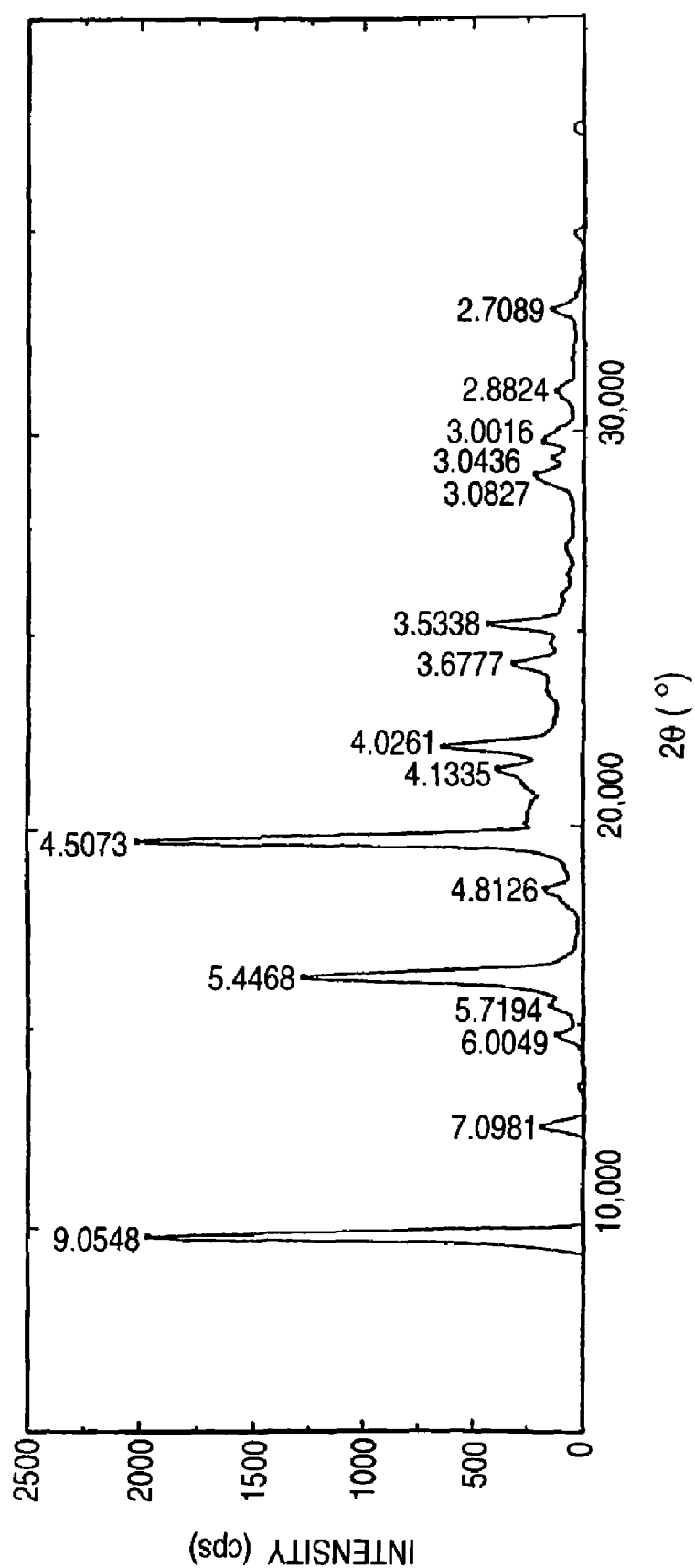
FIG. 2 shows a powder X-ray diffraction spectrum of 2-(4-(3-cyclopentyloxy-4-difluoromethoxyphenyl)-4-cyanopiperidin-1-yl)acetic acid (comparative compound).

The powder X-ray diffraction spectrum charts are shown in FIG. 1 and FIG. 2, which are given by Cu Kα characteristic X-ray of compound 1 and the comparative compound. In the powder X-ray diffraction spectrum, its grid interval and relative intensity are shown in table 1.

Conditions for Measurement:

| Apparatus: | Rigaku corporation, RINT-1400 powder X-ray diffraction apparatus |
|---|---|
| Target: | Cu |
| Filter: | not used |
| Power Voltage: | 40 kV |
| Power Current: | 20 mA |
| Scanning Speed: | 2.0°/min |

TABLE 1

Powder X-ray diffraction relative intensity

| Compound 1 (FIG. 1) | | The comparative compound (FIG. 2) | |
|---|---|---|---|
| Grid Interval (Å) | Relative intensity | Grid Interval (Å) | Relative intensity |
| 9.00 | 56 | 9.05 | 98 |
| 6.29 | 19 | 7.10 | 9 |
| 5.70 | 39 | 6.00 | 5 |
| 5.15 | 30 | 5.72 | 7 |
| 5.04 | 81 | 5.45 | 64 |
| 4.87 | 8 | 4.81 | 8 |
| 4.67 | 78 | 4.51 | 100 |
| 4.49 | 21 | 4.13 | 19 |
| 4.23 | 46 | 4.03 | 31 |
| 4.15 | 100 | 3.68 | 16 |
| 3.89 | 23 | 3.53 | 21 |
| 3.83 | 20 | 3.08 | 11 |
| 3.59 | 75 | 3.04 | 7 |
| 3.51 | 43 | 3.00 | 9 |
| 3.35 | 14 | 2.88 | 6 |
| 2.98 | 21 | 2.71 | 7 |
| 2.94 | 12 | | |
| 2.85 | 32 | | |
| 2.77 | 9 | | |

FIGS. 1 and 2 (table 1) illustrate that these two compounds are distinguished as having different crystal structures.

2) IR Data

Figure 3:
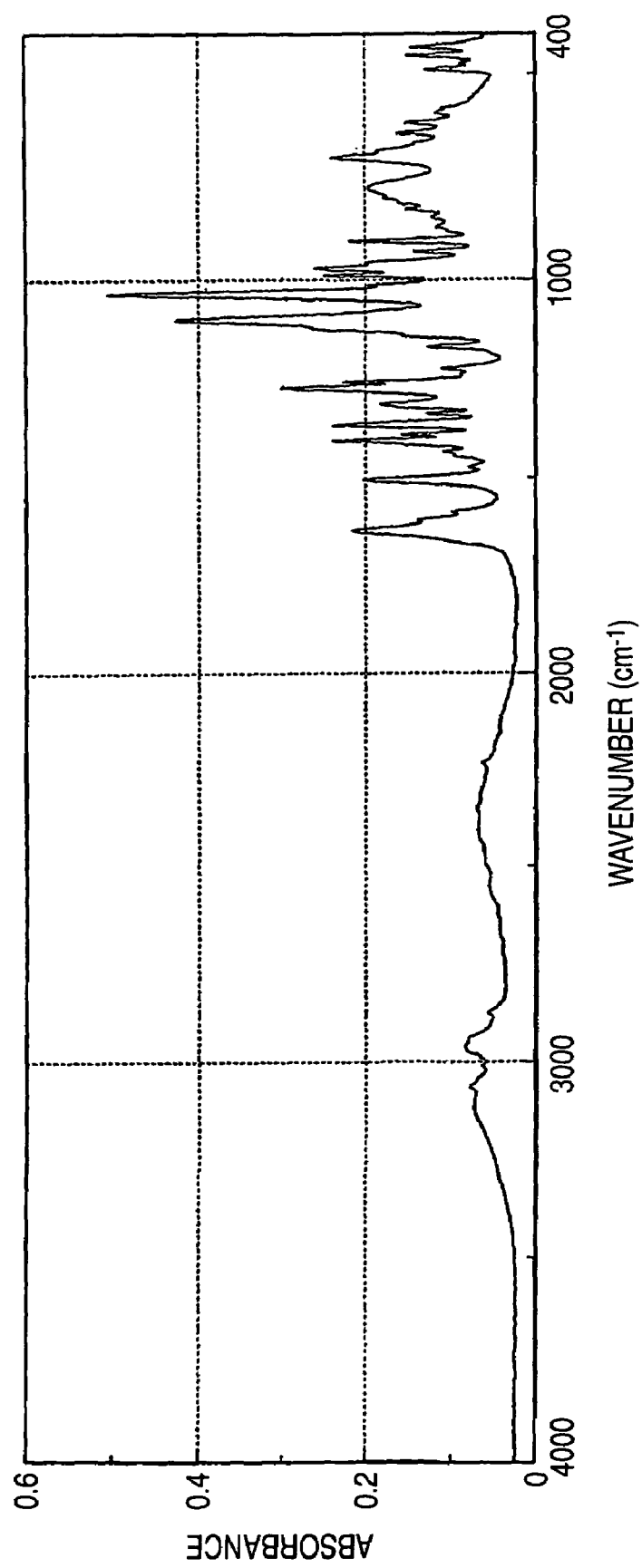
FIG. 3 shows IR spectrum data of compound 1.
Figure 4:
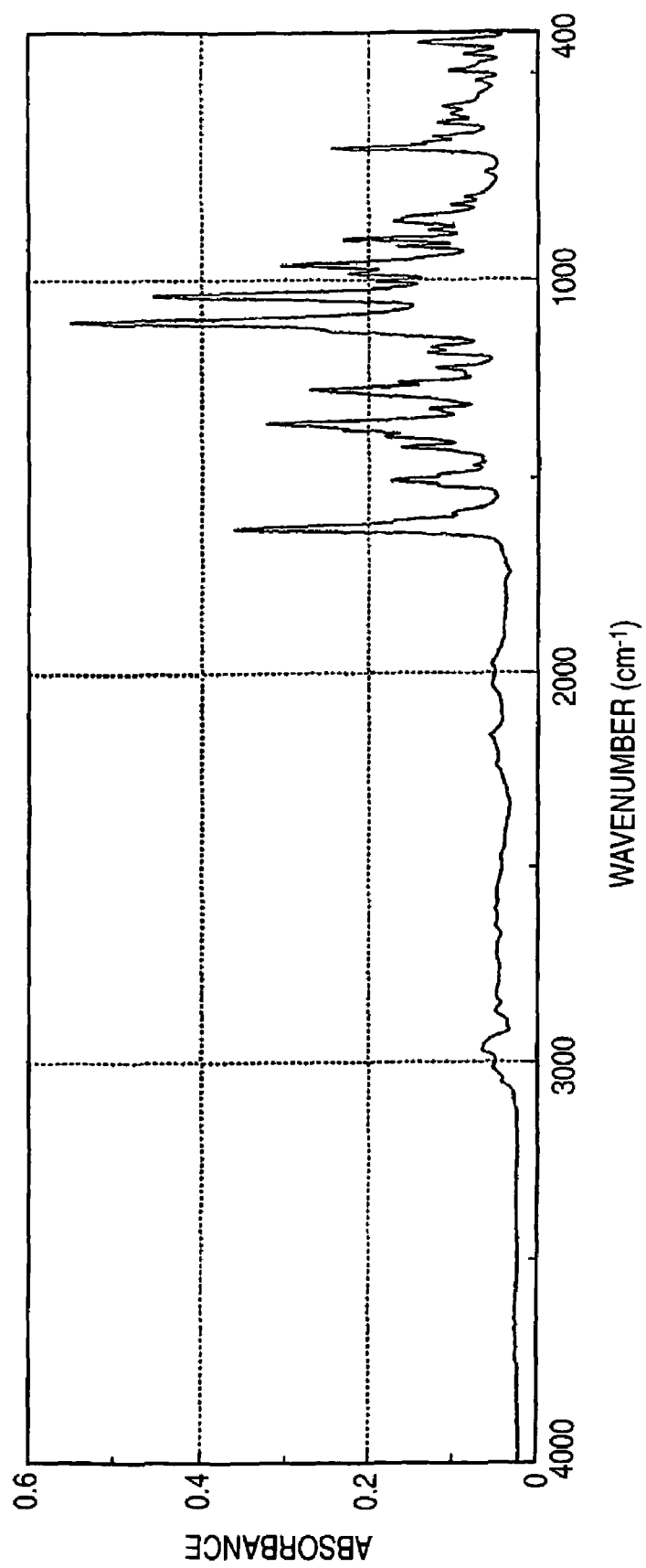
FIG. 4 shows IR spectrum data of the comparative compound.
Figure 5:
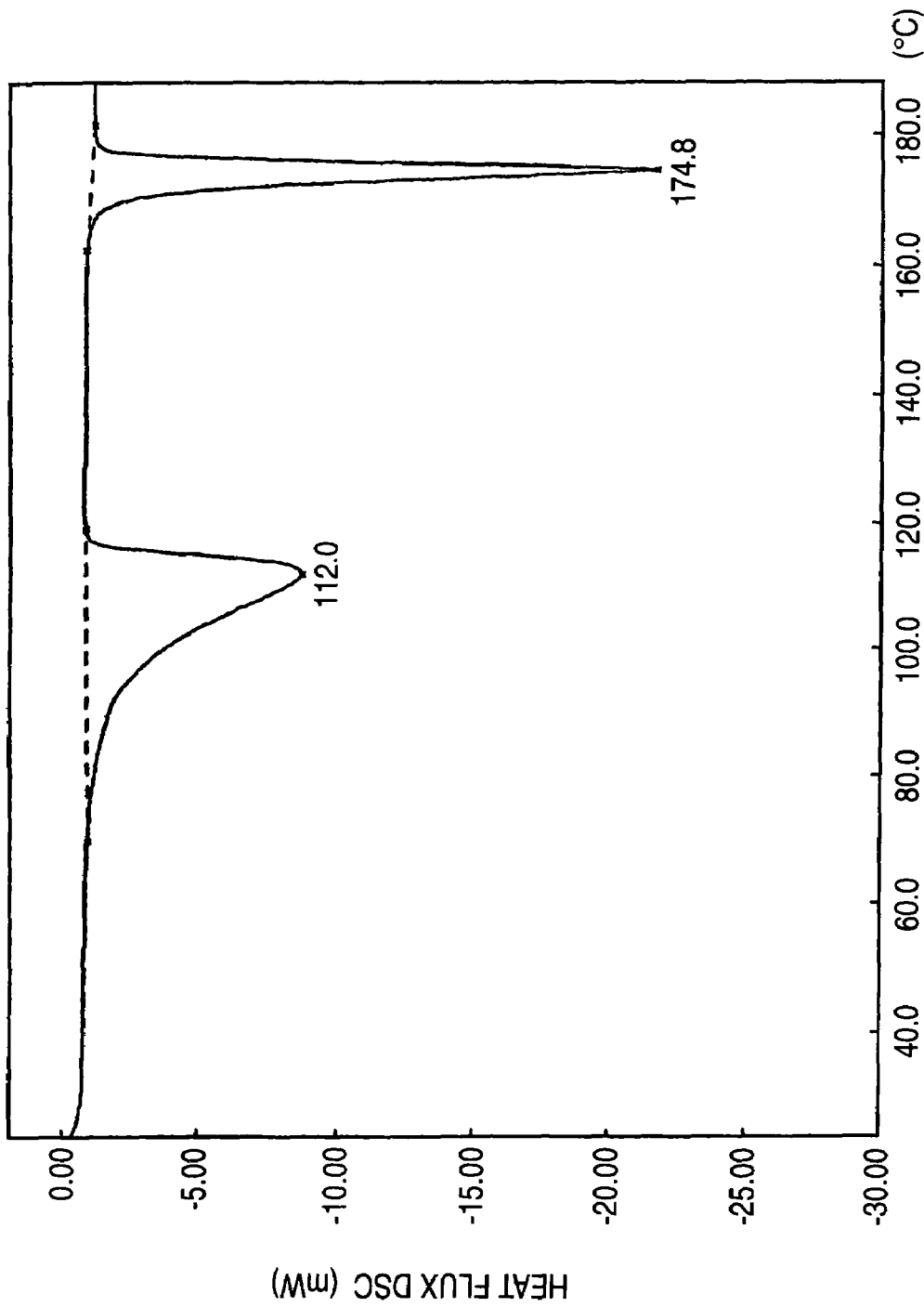
FIG. 5 shows DSC measurement chart of compound 1.
Figure 6:
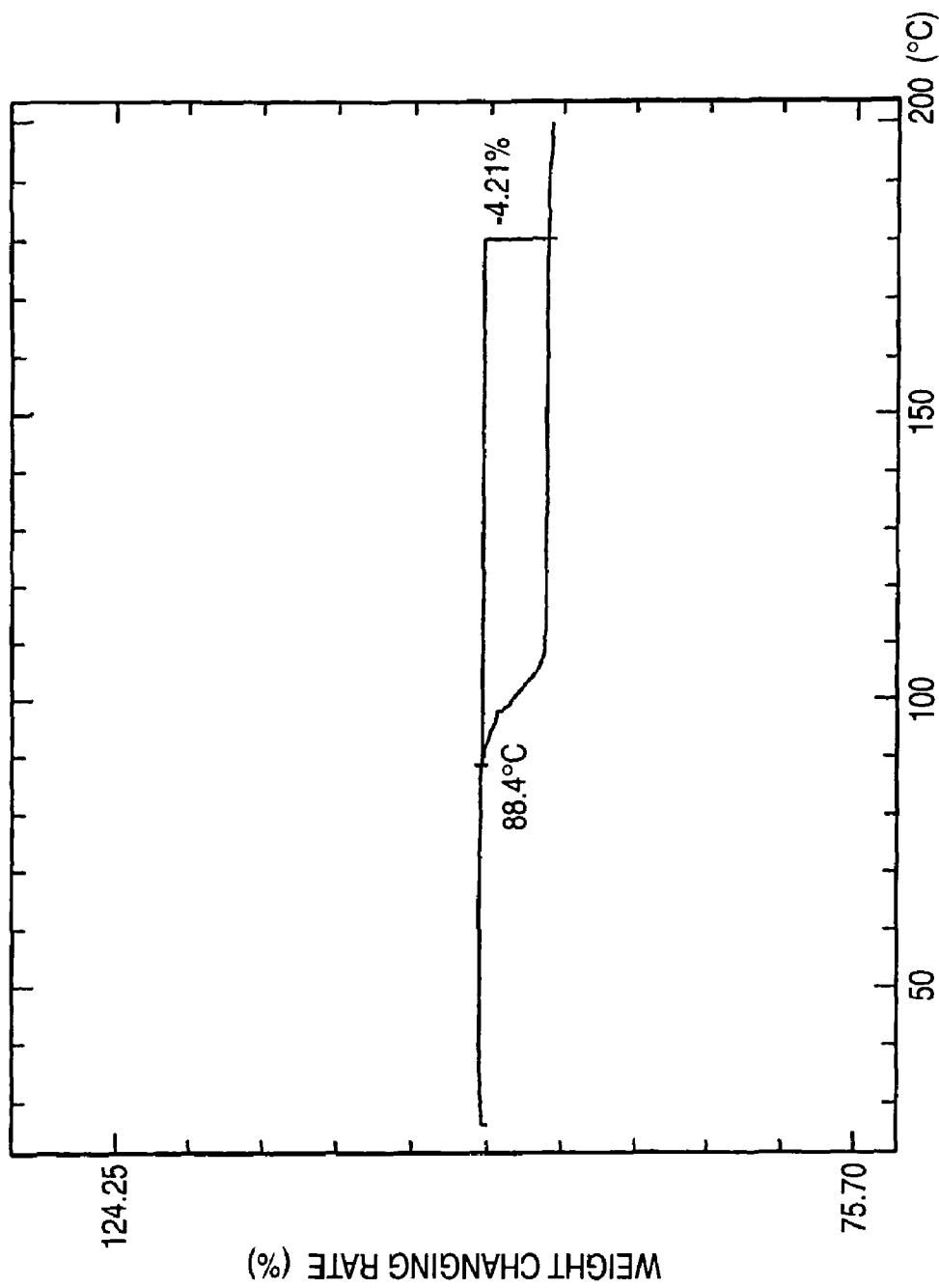
FIG. 6 shows TG measurement chart of compound 1.
Figure 7:
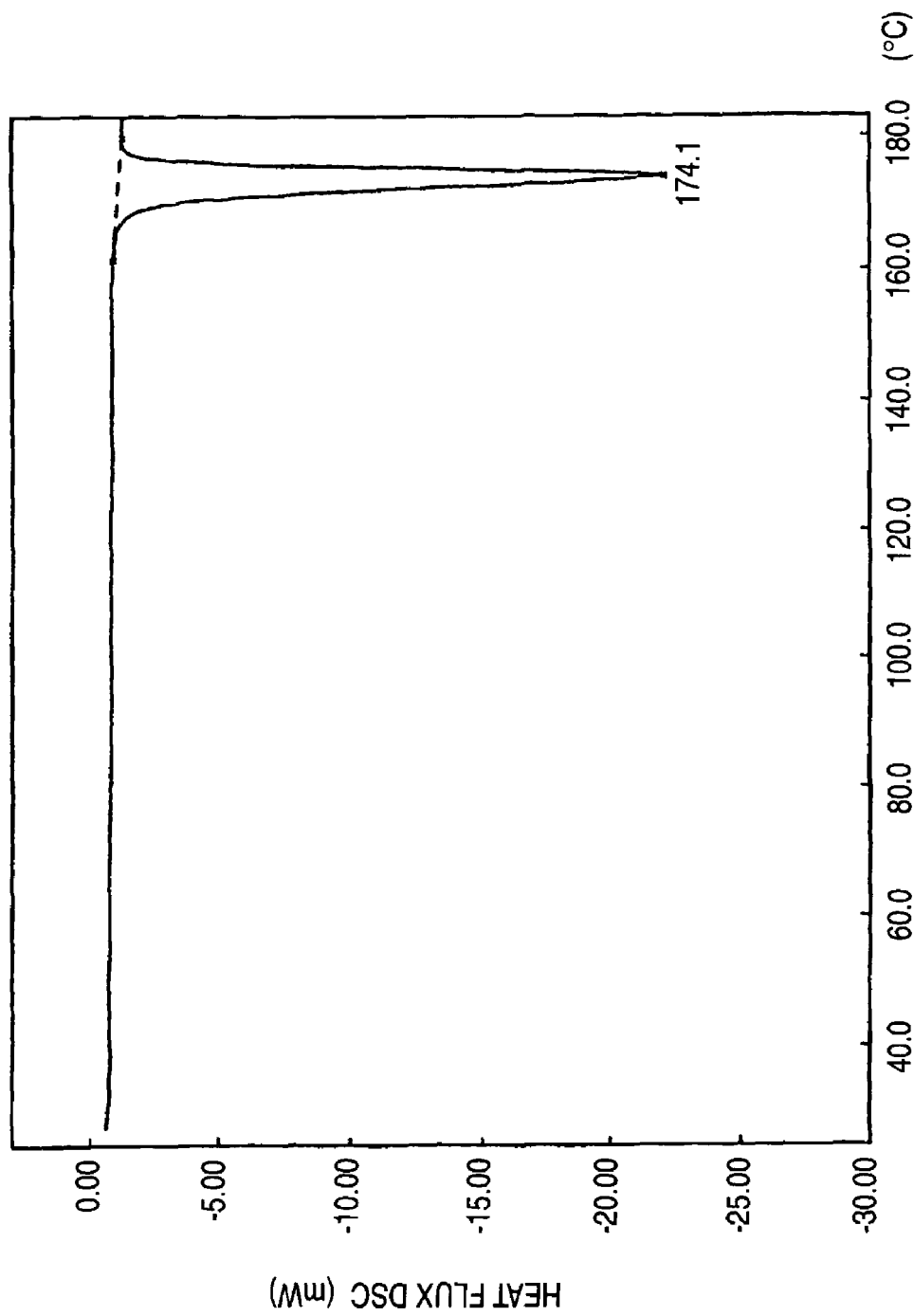
FIG. 7 shows DSC measurement chart of the comparative compound.
Figure 8:
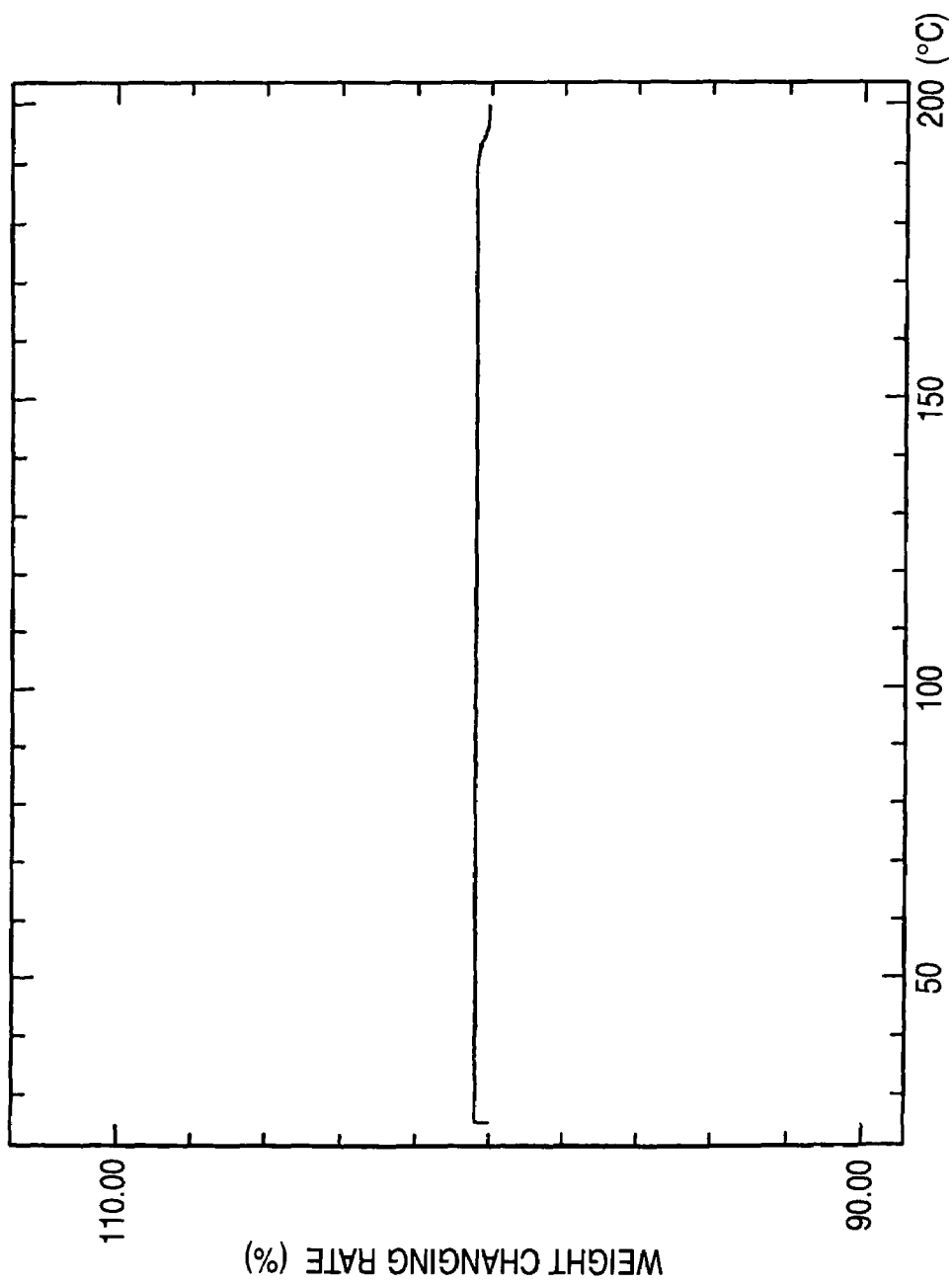
FIG. 8 shows TG measurement chart of the comparative compound.

FIGS. 3 and 4 show the IR spectra data of the compound 1 and the comparative compound.

Condition for Measurement:

| Apparatus: | JASCO Corporation FT/IR-660Plus Infrared dispersion photometer |
|---|---|
| Dissolution performance: | 4 cm$^{-1}$ |
| Scanning number of times: | 64 |

To compare FIG. 3 with FIG. 4, since the absorption peaks between 1450 and 1200 cm$^{-1}$ and between 900 and 600 cm$^{-1}$ are different in particular, these two compounds are apparently different.

3) DSC Data and TG Data

FIGS. 5, 6, 7 and 8 show DSC and TG measurement charts of compound 1 and the comparative compound.

Conditions for Measurement:

DSC

| | |
|---|---|
| Apparatus: | Seiko Instruments DSC6200 differential scanning calorimeter |
| Sample: | ca. 4.8 mg |
| Sample cell: | aluminum open cell |
| Argon gas flow: | 20 ml/min |
| Heating rate: | 10° C./min. |

TG

| | |
|---|---|
| Apparatus: | Shimadzu TGA-50 thermogravimetric analyzer |
| Sample: | ca. 4.8 mg |
| Sample cell: | aluminum open cell |
| Nitrogen gas flow: | 20 ml/min, |
| Heating rate: | 10° C./min. |

In DSC data and TG data, they are apparently different.

In compound 1, DSC data (FIG. 5) showed a broad endothermic peak between 75 and 120° C. and an endothermic peak at 174° C. TG data (FIG. 6) showed a reduction in weight of 4.2% (corresponding to one molecule of water) in the former range and no reduction in weight was recognized until the temperature when the latter endotherm ceased.

In contrast, in the comparative compound, DSC data (FIG. 7) showed a single endothermic peak at 174° C. and no reduction in weight was recognized until the endotherm ceased.

Since the powder X-ray diffraction data of the two compounds (FIGS. 1 and 2) are different, it is conceivable that the peak between 75° C. and 120° C. is an endotherm by evaporation of water and crystal transition and it is considered that the endothermic peak at 174° C. resulted from melting.

4) Elementary Analysis Data

Elementary analysis data of compound 1 and the comparative compound is shown below.

Conditions for measurement:

| | |
|---|---|
| Apparatus: | Parkin Elmer PE2400 series II CHNS/O elementary analyzer |
| Sample: | 1.661 mg (the compound of the present invention of formula (I)) |
| | 1.606 mg (the comparative compound) |
| Combustion temperature: | 975° C. |
| Reduction Temperature: | 500° C. |
| Detector oven temperature: | 82.5° C. |
| Carrier gas: | high-purity helium gas, high-purity oxygen gas (99.999%) |
| Standard: | acetanilide |

| Compound 1 ($C_{20}H_{24}F_2N_2O_4 \cdot 1H_2O$) | |
|---|---|
| Calculated: | C, 58.24%; H, 6.35%; N, 6.79%. |
| Found: | C, 58.09%; H, 6.20%; N, 6.73%. |
| Comparative compound ($C_{20}H_{24}F_2N_2O_4$) | |
| Calculated; | C, 60.91%; H, 6.13%; N, 7.10%. |
| Found; | C, 60.90%; H, 5.90%; N, 7.09%. |

From these data, it is found that compound 1 is monohydrate and the comparative compound is anhydrate.

5) Single Crystal X-ray Structural Analysis Data

Figure 9:
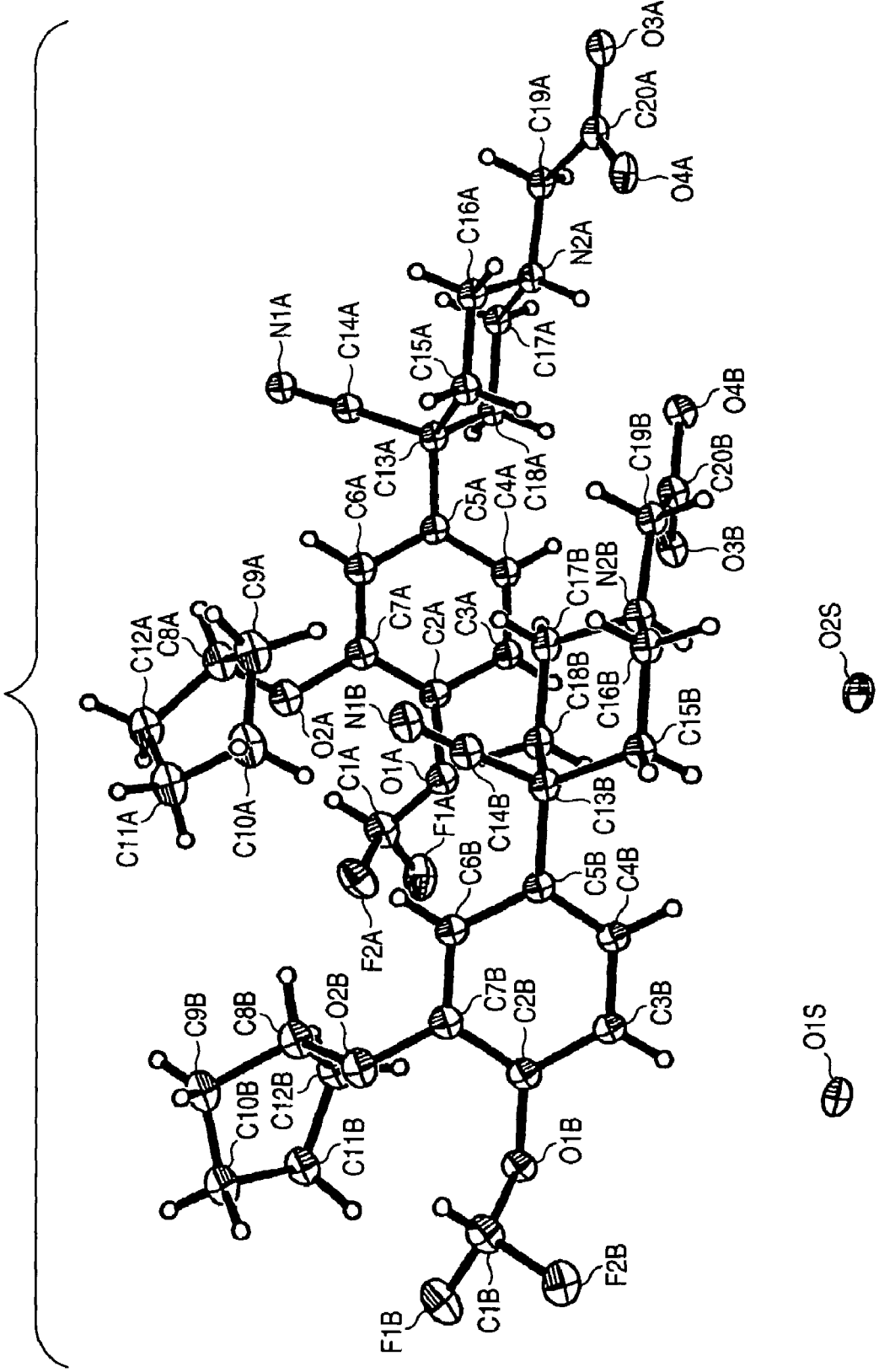
FIG. 9 shows single crystal structural analysis data of compound 1.

FIG. 9 and show the data of single X-ray structural analysis of compound 1.

Conditions for Measurement:

| | |
|---|---|
| Apparatus: | Bruker SMART6000 CCD single crystal structural analyzer |
| Temperature on measurement: | 100K |
| Target: | Mo ($\lambda = 0.71073$ Å) |
| R = 0.1390 | |

Crystal Data are as Follows:

| | |
|---|---|
| Lattice multiplier: | a = 11.9387(13)Å, b = 35.127(4)Å, c = 14.8284(16)Å, β = 141.418(3)°, V = 3878.1(7)Å$^3$ |
| Space group: | P2$_1$/n |
| | Z = 8 |

Figure 10:
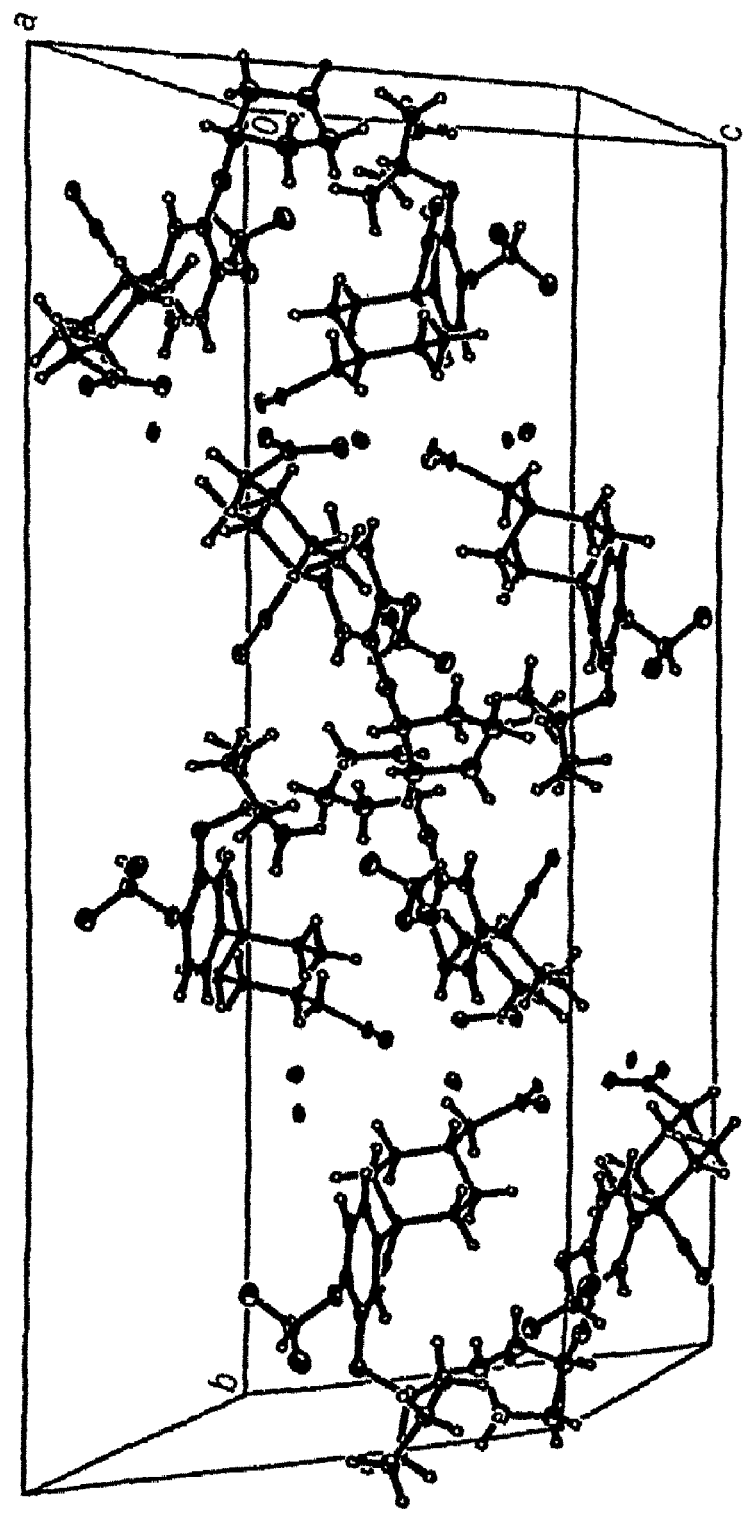
FIG. 10 shows single crystal structural analysis data of compound 1.

From FIGS. 9 and 10, it is apparent that compound 1 is monohydrate.

Pharmacological Activity:

The PDE4 inhibitory activity of the compounds of the present invention of formula (I) was confirmed by the following tests.

In vitro Enzyme Assay

Experimental Methods:

U937 cells (derived from human monocyte) were cultured in PRMI 1640 medium containing 10% bovine fetal serum. The U937 cells were harvested and homogenized in 50 mM Tris-HCl buffer [pH 7.5, containing PMSF (1 mM), leupeptin (1 μg/ml) and pepstatin A (1 μg/ml)]. After centrifugation (at 15,000 rpm for 10 minutes), the supernatant was recovered and filtered through a 0.45 μm filter. The sample was applied to MonoQ (manufactured by Pharmacia, strong anion exchange resin) column and eluted by a density gradient of 0 to 0.8 M NaCl. Fractions from which the PDE activity was disappeared by 10 μM rolipram (a PDE4-selective inhibitor) were recovered and used as the enzyme solution for the measurement of PDE4 inhibitory activity.

The enzyme activity was measured by the following method. 70 μl of a diluted enzyme solution (in phosphate buffer (pH 7.4) containing 0.1 mg/kg bovine serum albumin), 10 μl of a solution of compound 1 (in 10% DMSO) and 10 μl of $^3$H-cAMP (20,000 cpm, 10 μM) [in an imidazole buffer (100 mM, pH 7.5) containing MgSO$_4$ (100 mM) and bovine serum albumin (1 mg/ml)] were mixed and incubated at room temperature for 30 minutes. The reaction was stopped by treating the reaction solution for 2.5 minutes in a microwave oven. After centrifugation (at 2,000 rpm for 1 minute), 10 μl of snake venom (1 mg/ml, manufactured by Sigma, trade name V7000) was added and incubated for 30 minutes at room temperature. To an alumina column (100 μl), was applied 50 μl of the supernatant, eluted with 80 μl of 0.005 N hydrochloric acid, and radioactivity of the eluate was measured.

PDE4 inhibitory activity ratio of the compound of the present invention of formula (I) was calculated by the following equation:

PDE4 activity inhibitory ratio (%)=(1−radioactivity in the presence of the compound of the present invention of formula (1)/radioactivity in the absence of the compound of the present invention of formula (I))×100

$IC_{50}$ was calculated as a concentration of compound 1 of 50% inhibition of PDE4 activity.

As a result, the $IC_{50}$ value of compound 1 was 42 nmol/l.

TNF-α Production Inhibitory Effect:

A heparinized blood sample collected from a healthy person was dispensed in 180 μl/well into a 96-well plate. A solution of compound 1 (final concentration of DMSO: 0.1% or less) was dispensed at 10 μl and the plate was allowed to stand at 37° C. for 30 minutes in a 5% $CO_2$ incubator. The reaction was initiated by adding 10 μl of LPS solution. After 6 hours of incubation in a $CO_2$ incubator (5% $CO_2$, humidified), the plate was shaken and then centrifuged at 300×g for 5 minutes to recover 50 μl of the supernatant (blood plasma). The amount of TNF-α in the supernatant was measured using a human TNF-α ELISA kit (DIACLONE Cat. No. 850.090.096) in accordance with the method attached thereto. As a result, compound of 1 showed a dose-dependent inhibitory activity against TNF-α production.

Toxicity:

The toxicity of the compound of the present invention of formula (I) is very low so that it is considered that the compound is sufficiently safe for using as a pharmaceutical.

Application to Pharmaceutical:

Since the compound of the present invention of formula (I) has PDE4 inhibitory activity, it is considered to be useful in preventing and/or treating various diseases such as inflammatory diseases (e.g., asthma, chronic obstructive pulmonary diseases, sepsis, sarcoidosis, nephritis, hepatitis, enteritis, etc.), diabetic diseases, allergic diseases (e.g., allergic rhinitis, atopic dermatitis, etc.), autoimmune diseases (e.g., ulcerative colitis, Crohn's disease, rheumatism, psoriasis, multiple sclerosis, collagen disease, etc.), ocular diseases (e.g. allergic conjunctivitis, seasonal conjunctivitis, etc.), osteoporosis, bone fracture, osteoarthritis, obesity, bulimia, depression, Parkinson's disease, dementia, ischemic reperfusion injury, leukemia, AIDS, shock, systemic inflammatory responsive diseases (SIRS), etc.

The compound of the present invention of formula (I) is generally administered systemically or topically and orally or parenterally when it is used for the above objects.

The compound of formula (I) may also be administered as a concomitant agent in combination with other agents for 1) supplementing and/or reinforcement of preventive and/or treating effect(s) of the compound,
2) improvement in kinetics and absorption of the compound and reduction of dose and/or
3) reduction of side effect of the compound.

A concomitant agent of the compound of formula (I) with other agents may be administered in a mode of compounded agent in which both components are compounded in a single preparation or in a mode of separate preparations. When administration is conducted using separate preparations, a simultaneous administration and administrations with time difference is included. In the case of administrations with time difference, the compound of formula (I) may be firstly administered and then other drug may be administered, or the other drug may be firstly administered and then the compound of formula (I) may be administered. Each of the methods for the administration may be the same or different.

There is no particular limitation for the diseases for which the above-mentioned concomitant agent achieves the preventive and/or the treating effect but any disease will be acceptable so far as it supplements and/or enforces the preventive and/or treating effect of the compound of formula (I).

For example, examples of the other drug for supplementing and/or reinforcing the preventive and/or treating effect of the compound of formula (I) to asthma and/or chronic obstructive pulmonary diseases include, for example, steroidal agents, $β_2$ adrenergic receptor stimulators, leukotriene receptor antagonists, thromboxane synthase inhibitors, thromboxane $A_2$ receptor antagonists, mediator liberation inhibitors, antihistamines, xanthine derivatives, anticholinergic agents, cytokine inhibitors, prostaglandins, forskolin formulations, elastase inhibitors, metalloprotease inhibitors, expectorants, antibiotics, etc.

For example, examples of the other drug for supplementing and/or reinforcing the preventive and/or treating effect of the compound of formula (I) to allergic rhinitis include, for example, antihistamines, mediator liberation inhibitors, thromboxane synthase inhibitors, thromboxane $A_2$ receptor antagonists, leukotriene receptor antagonists, steroidal agents, $β_2$ adrenergic receptor stimulators, xanthine derivatives, anticholinergic agents, etc.

For example, examples of the other drug for supplementing and/or reinforcing the preventive and/or treating effect of the compound of formula (I) to osteoporosis and/or bone fracture include, for example, bisphosphonates, vitamin D agents, calcium supplements, estrogen agents, calcitonin agents, isoflavone agents, protein anabolic steroids, vitamin K agents, prostaglandins, cathepsin K inhibitors, etc.

For example, examples of the other drug for supplementing and/or reinforcing the preventive and/or treating effect of the compound of formula (I) to ulcerative colitis and/or Crohn's disease include, for example, prostaglandin synthase inhibitors, steroidal agents, immunosuppressants, leukotriene receptor antagonists, TNFα antagonists, cell adhesion molecule inhibitors, 5-lipoxygenase inhibitors, elastase inhibitors, metalloprotease inhibitors, etc.

For example, examples of the other drug for supplementing and/or reinforcing the preventive and/or treating effect of the compound of formula (I) to rheumatism include, for example, non-steroidal anti-inflammatory diseases, disease modifying anti-rheumatic drugs (slow-acting antirheumatic drugs), steroidal agents, immunosuppressants, antiphlogistic enzyme, cartilage-protective agents, T cell inhibitors, TNFα inhibitors, prostaglandin synthase inhibitors, IL-6 inhibitors, interferon γ agonists, IL-1 inhibitors, prostaglandins, etc.

Steroidal agents include the followings.

For example, external medicines include, clobetasol propionate, diflorasone diacetate, fluocinonide, monometasone furoate, betamethasone dipropionate, betamethasone butyrate propionate, betamethasone valerate, difluprednate, budesonide, diflucortolone valerate, amcinonide, halcinonide, dexamethasone, dexamethasone, dexamethasone, dexamethasone, hydrocortisone acetate, hydrocortisone lactate, hydrocortisone lactate propionate, deprodone propionate, prednisolone valerate-acetate, fluocinolone acetonide, beclometasone dipropionate, triamcinoloneacetonide, flumetasone pivalate, alclometasone dipropionate, clobetasone butyrate, prednisolone, beclometasone propionate, fludroxycortide, etc.

For example, internal agents and/or agents for injection include, cortisone acetate, hydrocortisone, hydrocortisone sodium phosphate, hydrocortisone sodium succinate, fludrocortisone acetate, prednisolone, prednisolone acetate, prednisolone sodium succinate, butylprednisolone acetate, prednisolone sodium phosphate, halopredone acetate, methylprednisolone, methylprednisolone acetate, prednisolone sodium succinate, triamcinolone, triamcinolone acetate, triamcinolone acetonide, dexamethasone, dexamethasone acetate, dexamethasone sodium phosphate, dexamethasone palmitate, paramethasone acetate, betamethasone, etc.

For example, inhalant agents include, beclomethasone, fluticasone propionate, Budesonide, flunisolide, triamcinolone, ST-126P, ciclesonide, dexamethasone palmitate, mometasone furoate, prasterone sodium sulfate, deflazacort, methyl predonisolone, methyl predonisolone sodium succinate, etc.

Non-steroidal anti-inflammatory drugs include, for example, sasapyrine (salitylosalitylic acid), sodium salicylate, aspirin, aspirin dialuminate, diflunisal, indomethacin, suprofen, ufenamate, dimethylisopropylazulene, bufexamac, felbinac, dichlofenac, tolmetin sodium, clinoril, fenbufen, nabumetone, proglumetacin maleate, indometacin farnesil, acemetacin, proglumetacin maleate, amfenac sodium, mofezolac, etodolac, ibuprofen, ibuprofenpiconol, naproxen, flurbiprofen, flurbiprofen axetil, ketoprofen, phenoprofen calcium, tiaprofenic acid, oxaprozin, pranoprofen, loxoprofen sodium, alminoprofen, zaltoprofen, mefenamic acid, aluminum mefenamate, tolfenamic acid, floctafenine, ketophenylbutazon, oxyfenbutazon, piroxicam, tenoxicam, ampiroxicam, napageln ointment, epirizole, tiaramide, hydrochloride, tinoridine hydrochloride, emorfazone, sulpyrine, migrenin, saridon, cedes G, amipylo-N, sorbon, pyrine cold preparation, acetoaminofen, fenacetin, dimetotiazine mesilate, simetride, non-pyrine cold preparation, etc.

Immunosuppressants include, for example, Protopic (FK506), methotrexate, cyclosporin, ascomycin, leflunomide, bucillamine, salazosulfapyridine, etc.

Prostaglandins (abbreviated as PG hereafter) include PG receptor agonist, PG receptor antagonist, etc.

PG receptor includes, PGE receptors ($EP_1$, $EP_2$, $EP_3$, $EP_4$), PGD receptor (DP), PGF receptor (FP), PGI receptor (IP), etc.

Mediator liberation inhibitors include, for example, tranilast, sodium cromoglicate, amlexanox, repirinast, ibudilast, tazanolast, pemilolast potassium, etc.

Antihistamine agents include, for example, ketotifen fumarate, mequitazine, azelastine hydrochloride, oxatomide, terfenadine, emedastine difumarate, epinastine hydrochloride, astemizole, ebastine, cetirizine hydrochloride, bepotastine, fexofenadine, loratadine, desloratadine, olopatadine hydrochloride, TAK-427, ZCR-2060, NIP-530, mometasone furoate, mizolastine, BP-294, andolast, auranofin, acrivastin, etc.

$β_2$-Adrenergic receptor stimulators include, for example, fenoterol hydrobromide, salbutamol sulfate, terbutaline sulfate, formoterol fumarate, salmeterol xinafoate, isoproterenol sulfate, orciprenaline sulfate, clorprenaline sulfate, epinephrine, trimetoquinol hydrochloride, hexoprenaline sulfate, procaterol hydrochloride, tulobuterol hydrochloride, tulobuterol, pirbuterol hydrochloride, clenbuterol hydrochloride, mabuterol hydrochloride, ritodrine hydrochloride, bambuterol, dopexamine hydrochloride, meluadrine tartrate, AR-C68397, levosalbutamol, R,R-formoterol, KUR-1246, KUL-7211, AR-C89855, S-1319, etc.

Leukotriene receptor antagonists include, for example, pranlukast hydrate, montelukast, zafirlukast, seratrodast, MCC-847, KCA-757, CS-615, YM-158, L-740515, CP-195494, LM-1484, RS-635, A-93178, S-36496, BIIL-284, ONO-4057, etc.

Thromboxane synthase inhibitors include, for example, ozagrel hydrochloride, imitrodast sodium, etc.

Thromboxane $A_2$ receptor antagonists include, for example, seratrodast, ramatroban, domitroban calcium hydrate, KT-2-962, etc.

Xanthine derivatives include, for example, aminophylline, theophylline, doxophylline, dipamphylline, diprophylline, etc.

Anticholinergic agents include, for example, ipratropium bromide, oxitropium bromide, flutropium bromide, cimetropium bromide, temiverine, tiotropium bromide, revatropate (UK-112166), etc.

Cytokine inhibitors include, for example, suplatast tosylate (product name IPD), etc.

Other phosphodiesterase inhibitors include, for example, PDE4 inhibitors, i.e. rolipram, cilomilast (Produc Name: Alifro), Bay19-8004, NIK-616, cilomilast (BY-217), cipamphiline (BRL-61063), atizolam (CP-80633), SCH-351591, YM-976, V-11294A, PD-168787, D-4396, IC-485, etc.

Prostaglandin synthase inhibitors include, for example, salazosulfapyridine, mesalazine, osalazine, 4-aminosalicylic acid, JTE-522, auranofin, carprofen, diphenpyramide, flunoxaprofen, flurbiprofen, flurbiprofen, indomethacin, ketoprofen, lornoxicam, loxoprofen, meloxicam, oxaprozin, persarmide, piproxen, piroxicam, piroxicam beta-cyclodextrin complex, piroxicam cinnamate, zaltoprofen, pranoprofen, etc.

Expectorants include, for example, foeniculated ammonia, sodium bicarbonate, bromhexine hydrochloride, carbocysteine, ambroxol hydrochloride, ambroxol hydrochloride sustained release formulation, methylcysteine hydrochloride, acetylcysteine, L-ethylcysteine hydrochloride, tyloxapol, etc.

Bisphosphonates include, for example, alendronate sodium, clodronate disodium, pamidronate sodium, etidronate disodium, ibandronate, incadronate disodium, minodronate, orpadronate, risedronate sodium, tiludronate, zoledronate, etc.

Calcitonin agents include, for example, calcitonin, elcatonin, etc.

Antiphlogistic enzymes include, for example, lysozyme chloride, bromelain, pronase, serrapeptase, concomitant formulation of streptokinase and streptodornase, etc.

Disease modifying anti-rheumatic drugs (slow-acting anti-rheumatic drugs) include for example, aurothioglucose, sodium aurothiomalate, auranofin, actarit, D-penisillamine agent, lobenzarit disodium, bucillamine, hydroxychloroquine, salazosulfapyridine, etc.

Cartilage protective agents include, for example, sodium hyaluronate etc.

There is no limitation for the ratio by weight of the compound of formula (I) to other agent.

With regard to other agents, two or more members of any agent may be administered in combination.

Such other agents which supplement and/or reinforce the preventive and/or treating effect of the compound of formula (I) include not only those which have been found on the basis of the above-mentioned mechanism but also those which will be found in future.

The compound of the present invention of formula (I), a combination of the compound of the present invention of formula (I) and other drug is generally administered systemically or topically and orally or parenterally when it is used for the above objects.

The dosages are determined depending on age, body weight, symptom, therapeutic effect, administration route, duration of the treatment and the like. Generally, 1 mg to 1000 mg per adult is orally administered once to several times per day, or 1 mg to 100 mg per adult is parenterally administered (preferably by intravenous administration) once to several times per day, or continuously administered from vein for 1 to 24 hours per day.

Since the dose changes depending on various conditions as described above, there are cases in which doses lower than or greater than the above ranges may be used.

The compound of the present invention of formula (I) and concomitant agent of the compound of the present invention of formula (I) and other agent(s) may be administered in the form of solid compositions, liquid compositions and other compositions for oral administration, and injections, liniments, suppositories, eye lotions, inhalants and the like for parenteral administration.

Solid compositions for oral administration include tablets, pills, capsules, dispersible powders, granules and the like.

Capsules include hard capsules and soft capsules.

In such solid compositions, one or more active compound(s) are mixed with at least one inert diluent such as lactose, mannitol, glucose, hydroxypropyl cellulose, microcrystalline cellulose, starch, polyvinyl pyrrolidone or magnesium metasilicate aluminate. The composition may also contain additional substances other than the inert diluent, e.g., lubricants such as magnesium stearate, disintegrating agents such as cellulose calcium glycolate, stabilizing agents such as lactose, and assisting agents for dissolving such as glutamic acid and asparatic acid according to usual methods. If necessary, the tablets or pills may be coated with film of gastric- or enteric-coating agents such as sugar, gelatin, hydroxypropyl cellulose and hydroxypropyl cellulose phthalate, or be coated with two or more films. Furthermore, capsules of absorbable materials such as gelatin are included.

Liquid compositions for oral administration include pharmaceutically acceptable emulsions, solutions, syrups, elixirs and the like. In such liquid compositions, one or more active compound(s) are contained in an inert diluent commonly used (e.g., purified water, ethanol). Furthermore, such compositions may also contain auxiliary material such as wetting agents or suspending agents, sweetening agents, flavoring agents, flavoring agents, and preserving agents.

Other compositions for oral administration include sprays containing one or more active compound(s) which are prepared by known methods. Such compositions may contain stabilizing agents such as sodium hydrogen sulfate, buffering agents to give isotonicity, isotonic solutions such as sodium chloride, sodium citrate or citric acid, in addition to inert diluents. The processes for preparing sprays are described in U.S. Pat. Nos. 2,868,691 and 3,095,355.

Injections for parenteral administration in the present invention include sterile aqueous or non-aqueous solutions, suspensions and emulsions. Aqueous solutions and suspensions include distilled water for injection and physiological saline. Non-aqueous solutions and suspensions include propylene glycol, polyethylene glycol, plant oil such as olive oil, alcohols such as ethanol, POLYSORBATE80 (registered trade mark), and the like. Sterile aqueous and non-aqueous solutions, suspensions and emulsions may be used as a mixture. Such compositions may further contain preserving agents, wetting agents, emulsifying agents, dispersing agents, stabilizing agents (e.g., lactose), auxiliary agents such as solubilizing auxiliary agents (e.g., glutamic acid, aspartic acid). They may be sterilized by filtration through a bacteria-retaining filter, incorporation of a sterilizing agent or irradiation. For example, they may also be manufactured in the form of sterile solid compositions which can be dissolved in sterile water or other sterile diluent for injection before use of the freeze-dried product.

The dosage form of eye-drops for parenteral administration include eye lotions, suspending eye lotions, emulsion eye lotions, eye lotions dissolved when used, and eye ointments.

These eye drops are manufactured according to known methods. For example, the eye drops can be prepared, if necessary, by appropriately selecting isotonizing agents (e.g., sodium chloride, concentrated glycerine, etc.), buffering agents (e.g., sodium phosphate, sodium acetate, etc.), surfactants (e.g., POLYSORBATE80 (product name), polyoxyl 40 stearate, polyoxyethylene hydrogenated castor oil, etc.), stabilizing agents (sodium citrate, sodium edetate, etc.), preserving agents (e.g., benzalkonium chloride, paraben, etc.), and the like. They are sterilized in the final step or prepared by aseptic manipulation.

The inhalants for parenteral administration include aerosols, powders for inhalation, and liquids for inhalation, and the liquid for inhalation may be in the form which is dissolved or suspended in water or an appropriate medium when used.

These inhalations can be produced according to known methods.

For example, the liquids for inhalation can be prepared, if necessary, by appropriately selecting preserving agents (e.g., benzalkonium chloride, paraben, etc.), coloring agents, buffering agents (e.g., sodium phosphate, sodium acetate, etc.), isotonizing agents (e.g., sodium chloride, concentrated glycerine, etc.), thickeners (e.g., carboxyvinyl polymer, etc.), absorbefacients, and the like.

The powders for inhalation can be prepared, if necessary, by appropriately selecting lubricants (e.g., stearic acid, salts thereof, etc.), binding agents (e.g., starch, dextrin, etc.), excipients (e.g., lactose, cellulose, etc.), coloring agents, preserving agents (e.g., benzalkonium chloride, paraben, etc.), absorbefacients, and the like.

When the liquids for inhalation are administered, a sprayer (e.g., atomizer, nebulizer) is usually used. When the powders for inhalation are used, an inhalation administration apparatus for powder agents is usually used.

Other compositions for parenteral administration include liquids for external use, endemic liniments, ointments, suppositories for intrarectal administration, pessaries for intravaginal administration and the like containing one or more active compound(s) which can be prepared by known methods.

BEST MODE FOR CARRYING OUT THE INVENTION

The following reference examples and examples illustrate the present invention, but the present invention is not limited to them.

The solvents in the parentheses show the developing or eluting solvents and the ratios of the solvents used are by volume in chromatographic separations or TLC. The solvents in the parentheses in NMR show the solvents for measurement.

REFERENCE EXAMPLE 1

3-benzyloxy-4-hydroxybenzaldehyde

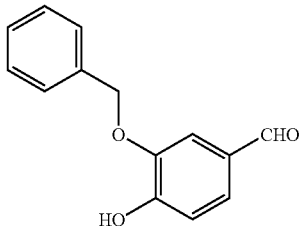

Under atmosphere of argon, to a suspension of sodium hydride (63%, 57.1 g) in anhydrous N,N-dimethylformamide (540 ml) was added a solution of 3,4-dihydroxybenzaldehyde (103.5 g) in anhydrous N,N-dimethylformamide (500 ml) dropwise slowly under cooling with ice. The reaction mixture was stirred for 30 minutes at room temperature, and to the mixture was added benzyl chloride (104 ml) under cooling with ice and it was stirred for 15 hours at room temperature. To the mixture was added water under cooling with ice, and was concentrated under reduced pressure. The residue was diluted by water and it was washed by methylene chloride. The methylene chloride layer was extracted by a 1N aqueous solution of sodium hydroxide. Combined aqueous layers were acidified by 2M hydrochloric acid and it was extracted by ethyl acetate. The organic layer was washed by a saturated aqueous solution of sodium chloride and dried over anhydrous sodium sulfate and concentrated. The residue was recrystallized from chloroform to give the title compound (99.4 g) having the following physical data.

TLC: 0.79 (chloroform:methanol=10:1);

NMR (CDCl$_3$): δ 9.82 (s, 1H), 7.52 (d, J=1.8 Hz, 1H), 7.49-7.35 (m, 6H), 7.07 (d, J=8.1 Hz, 1H), 6.28 (s, 1H), 5.18 (s, 2H).

REFERENCE EXAMPLE 2

3-benzyloxy-4-difluoromethoxybenzaldehyde

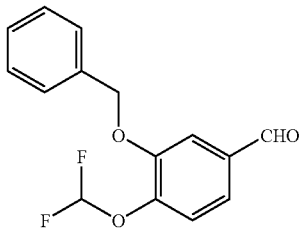

The compound prepared in reference example 1 (99.2 g) was dissolved in tetrahydrofuran (300 ml) and to the mixture was added 11N aqueous solution of sodium hydroxide (200 ml) at room temperature and it was stirred for 5 minutes at room temperature. The reaction solution was ventilated with chlorodifluoromethane at 60° C. (oil bath). After confirming that the starting material disappeared by thin layer chromatography on silica gel, the reaction solution was cooled to room temperature. To the reaction mixture was added water, extracted by diethyl ether. The organic layer was washed by 2N aqueous solution of sodium hydroxide, water, a saturated aqueous solution of sodium chloride successively, dried over anhydrous sodium sulfate and concentrated. The residue was purified by column chromatography on silica gel (hexane: ethyl acetate=6:1) to give the title compound (97.8 g) having the following physical data.

TLC: 0.83 (ethyl acetate:hexane=1:2);

NMR (CDCl$_3$): δ 9.92 (s, 1H), 7.57 (d, J=2.1 Hz, 1H), 7.51-7.31 (m, 7H), 6.69 (t, J=74.4 Hz, 1H), 5.21 (s, 2H).

REFERENCE EXAMPLE 3

3-benzyloxy-4-difluoromethoxybenzylalcohol

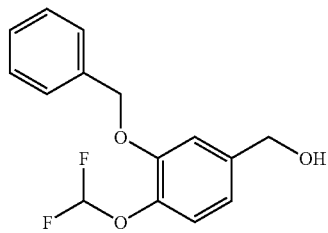

To a solution of the compound prepared in reference example 2 (97.8 g) in methanol (700 ml) was added sodium borohydride (9.8 g) under cooling with ice and the mixture was stirred for 15 minutes at 0° C. To the reaction mixture were added acetone and water, and the mixture was concentrated. To the mixture was added water and the mixture was extracted by ethyl acetate. The organic layer was washed by 2N hydrochloric acid, water and a saturated aqueous solution of sodium chloride successively, dried over anhydrous sodium sulfate and concentrated to give the title compound (105.48 g) having the following physical data. The given compound was used in the next reaction without subjecting to purification.

TLC: 0.40 (ethyl acetate:hexane=1:2);

NMR (CDCl$_3$): δ 7.46-7.30 (m, 5H), 7.16 (d, J=8.1 Hz, 1H), 7.08 (d, J=2.1 Hz, 1H), 6.92 (m, 1H), 6.57 (t, J=75.3 Hz, 1H), 5.15 (s, 2H), 4.65 (s, 2H), 1.61 (br, 1H).

REFERENCE EXAMPLE 4

3-benzyloxy-4-difluoromethoxybenzyl chloride

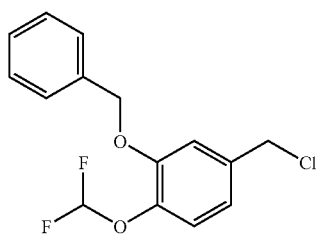

Under atmosphere of argon, to a solution of the compound prepared in reference example 3 (98.5 g) in methylene chloride (1760 ml) was added thionyl chloride (50.9 ml) dropwise under cooling with ice and the mixture was stirred for 3 hours at room temperature. The reaction mixture was concentrated. To the residue were added water and methylene chloride and extracted by methylene chloride. The organic layer was washed by a saturated aqueous solution of sodium bicarbonate and a saturated aqueous solution of sodium chloride successively, dried over anhydrous sodium sulfate and concentrated to give the title compound (135.45 g) having the following physical data. The compound was used in the next reaction without subjecting to purification.

TLC: 0.87 (ethyl acetate:hexane=1:2);

NMR (CDCl₃): δ 7.46-7.31 (m, 5H), 7.15 (d, J=8.4 Hz, 1H), 7.07 (d, J=2.1 Hz, 1H), 6.96 (dd, J=8.4, 2.1 Hz, 1H), 6.57 (t, J=75.0 Hz, 1H), 5.15 (s, 2H), 4.53 (s, 2H).

REFERENCE EXAMPLE 5

3-benzyloxy-4-difluoromethoxyphenylacetonitrile

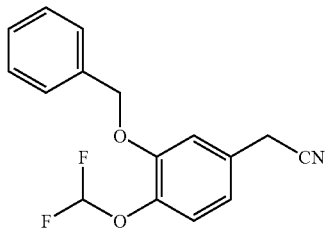

To a solution of the compound prepared in reference example 4 (135.4 g) in N,N-dimethylformamide (350 ml) was added sodium cyanide (52.6 g) and the mixture was stirred for 3 days at room temperature. To the reaction mixture was added water (1 L) and extracted by ethyl acetate (1 L+500 ml). The organic layer was washed by a saturated aqueous solution of sodium chloride (500 ml) and dried over anhydrous magnesium sulfate and concentrated. The residue was purified by column chromatography on silica gel (ethyl acetate:hexane=1:7→1:1) to give the title compound (92.69 g) having the following physical data.

TLC: 0.29 (ethyl acetate:hexane=1:4);

NMR (CDCl₃): δ 7.46-7.31 (m, 5H), 7.19 (d, J=8.1 Hz, 1H), 7.00 (d, J=2.1 Hz, 1H). 6.90 (dd, J=8.1, 2.1 Hz, 1H), 6.57 (t, J=75 Hz, 1H), 5.15 (s, 2H), 3.71 (s, 2H).

REFERENCE EXAMPLE 6

1-(3-benzyloxy-4-difluoromethoxyphenyl)cyclopent-3-encarbonitrile

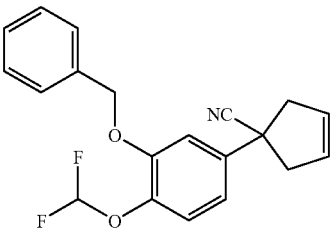

Under atmosphere of argon, to a solution of the compound prepared in reference example 6 (83 g) in tetrahydrofuran (717 ml) was added at −78° C. lithium bis(trimethylsilyl) amide (1.0 M in tetrahydrofuran, 717 ml) and the mixture was stirred for 1 hour. To the reaction mixture was added cis-1,4-dichloro-2-butene (30 ml) and the mixture was stirred for 1 hour at −78° C. and then stirred for 1.5 hours gradually warming to room temperature.

To the reaction mixture was added ice water (1 L) and it was extracted by ethyl acetate (1 L+500 ml). The organic layer was washed by 1N hydrochloric acid (250 ml×2) successively and dried over anhydrous magnesium sulfate and concentrated to give the title compound (99.8 g) having the following physical data.

TLC: 0.55 (ethyl acetate:hexane=1:2);

NMR (CDCl₃): δ 7.46-7.30 (m, 5H), 7.16 (d, J=8.4 Hz, 1H), 7.12 (d, J=2.1 Hz, 1H), 7.02 (dd, J=8.4, 2.1 Hz, 1H), 6.57 (t, J=75 Hz, 1H), 5.84-5.76 (m, 2H), 5.15 (s, 2H), 3.34-3.22 (m, 2H), 2.92-2.82 (m, 2H).

REFERENCE EXAMPLE 7

2-(4-(3-benzyloxy-4-difluoromethoxyphenyl)-4-cyanopiperidin-1-yl)acetic Acid Methyl Ester

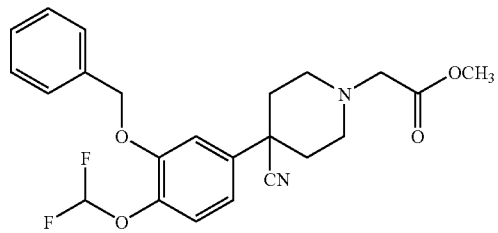

The compound prepared in reference example 6 (99.8 g) was dissolved in methanol (250 ml) and methylene chloride (400 ml) and at −78° C. to the mixture was ozone gas ventilated. The reaction mixture was stirred for 20 hours at −78° C. and to the mixture was added dimethylsulfide (21 ml) and the mixture was warmed to room temperature. The mixture was concentrated, and the residue was dissolved in N,N-dimethylformamide (800 ml) and to the mixture were added glycine methyl ester hydrochloride (72.0 g), acetic acid (172 ml) and sodium triacetoxyborohydride (182.4 g) and the mixture was stirred overnight at room temperature. To the reaction mixture was added a saturated aqueous solution of sodium bicarbonate (1 L) and the mixture was extracted by toluene (500 ml×2). The combined organic layer was washed by a saturated aqueous solution of sodium bicarbonate, water and a saturated aqueous solution of sodium chloride successively, dried over anhydrous magnesium sulfate and concentrated. The residue was purified by column chromatography on silica gel (ethyl acetate:hexane: toluene=4:6:1) to give the title compound (71.47 g) having the following physical data.

TLC: 0.39 (ethyl acetate:hexane=1:1);

NMR (CDCl₃): δ 7.36-7.12 (m, 7H), 7.07 (dd, J=8.4, 2.4 Hz, 1H), 6.58 (t, J=75 Hz, 1H), 5.14 (s, 2H), 3.76 (s, 3H), 3.32 (s, 3H), 3.12-3.04 (m, 2H), 2.72-2.61 (m, 2H), 2.25-2.13 (m, 2H), 2.10-2.01 (m, 2H).

REFERENCE EXAMPLE 8

2-(4-(3-hydroxy-4-difluoromethoxyphenyl)-4-cyanopiperidin-1-yl)acetic Acid Methyl Ester

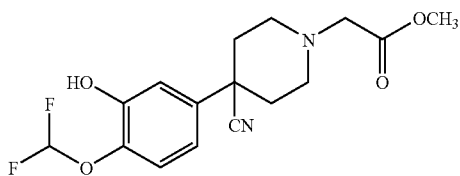

Under atmosphere of argon, to the compound prepared in reference example 7 (71.47 g) and 10% palladium carbon (containing 50% water, 15 g) was added ethyl acetate (100 ml) and under atmosphere of hydrogen the mixture was stirred for 3 hours at room temperature. The catalyst was filtered off over celite (registered trademark) and the filtrate was concentrated under reduced pressure to give the title compound (44.06 g) having the following physical data.

TLC: 0.30 (ethyl acetate:hexane=1:1);

NMR (CDCl$_3$): δ 7.16 (d, J=2.4 Hz, 1H), 7.13 (d, J=8.4 Hz, 1H), 7.02 (dd, J=8.4 Hz, 2.4 Hz, 1H), 6.54 (t, J=74.4 Hz, 1H), 3.76 (s, 3H), 3.32 (s, 2H), 3.11-3.03 (m, 2H), 2.71-2.60 (m, 2H), 2.25-2.14 (m, 2H), 2.11-2.03 (m, 3H).

REFERENCE EXAMPLE 9

2-(4-(3-cyclopentyloxy-4-difluoromethoxyphenyl)-4-cyanopiperidin-1-yl)acetic Acid Methyl Ester

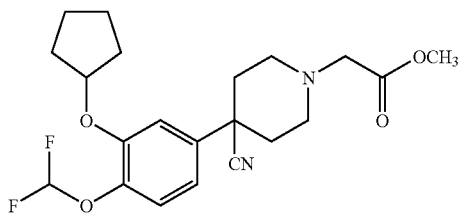

To a solution of the compound prepared in reference example 8 (15 g) in N,N-dimethylformamide (75 ml) were added potassium carbonate (15.2 g) and cyclopentyl bromide (7.1 ml) at room temperature, and it was stirred for 2 hours at 80° C. The reaction mixture was poured into ice-water (200 ml) and extracted by ethyl acetate. The organic layer was washed by a saturated aqueous solution of sodium chloride and dried over anhydrous magnesium sulfate and concentrated. The residue was purified by column chromatography on silica gel (ethyl acetate:hexane=1:2→1:1) to give the title compound (17.7 g) having the following physical data.

TLC: 0.34 (ethyl acetate:hexane=2:3);

NMR (CDCl$_3$): δ 7.16 (d, J=8.7 Hz, 1H), 7.10 (d, J=2.1 Hz, 1H), 7.03 (dd, J=8.7, 2.1 Hz, 1H), 6.54 (t, J=75.3 Hz, 1H), 4.86-4.79 (m, 1H), 3.76 (s, 3H), 3.33 (s, 2H), 3.13-3.05 (m, 2H), 2.72-2.62 (m, 2H), 2.27-2.17 (m, 2H), 2.12-2.04 (m, 2H) 2.00-1.60 (m, 8H).

REFERENCE EXAMPLE 10

4-(3-cyclopentyloxy-4-difluoromethoxyphenyl)-4-cyano-1-benzylpiperidine Hydrochloride

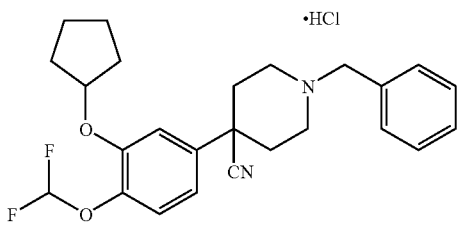

Thionyl chloride (16.8 ml) was dissolved in toluene (32.5 ml) and to the mixture was added a solution of N,N-bishydroxyethylbenzylamine (22.9 g) in toluene (32.5 ml) and the mixture was stirred for 1 hour at 60° C. To the reaction mixture were added water (50 ml) and 1N hydrochloric acid (50 ml) and the aqueous layer was separated. To the aqueous layer was added 3-cyclopentyloxy-4-difluoromethoxyphenylacetonitrile (described in WO 93/19750) (26.1 g) and then to the mixture were added 4N aqueous solution of sodium hydroxide (40 ml), sodium hydroxide (pellet, 120 g), tetrabutylammonium bromide (1.57 g) and the mixture was stirred for 1.5 hours at 90° C. To the reaction mixture were added tert-butyl methyl ether (250 ml) and water (125 ml). The organic layer was washed by water (250 ml) and 1N hydrochloric acid (40 ml) and concentrated. The residue was dissolved in methanol (250 ml) and it was added to 0.5N hydrochloric acid at 50° C. The reaction mixture was allowed to cool, then the precipitate was collected and washed by a mixture of methanol and water (1:2) (50 ml×2) and concentrated. The residue was dried under reduced pressure to give the title compound (36.5 g) having the following physical data.

TLC: 0.49 (toluene:ethyl acetate=10:1);

NMR (CD$_3$OD): δ 7.66-7.58 (m, 2H), 7.56-7.47 (m, 3H), 7.24-7.19 (m, 2H), 7.13-7.08 (m, 1H), 6.70 (t, J=75.0 Hz, 1H), 5.00-4.88 (m, 1H), 4.48 (s, 2H), 3.78-3.63 (m, 2H), 3.50-3.33 (m, 2H), 2.63-2.40 (m, 4H), 2.05-1.55 (m, 8H).

EXAMPLE 1

4-(3-cyclopentyloxy-4-difluoromethoxyphenyl)-4-cyanopiperidine Hydrochloride

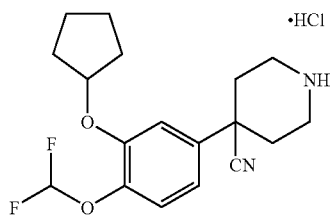

Under atmosphere of argon, to a solution of the compound prepared in reference example 10 (36.5 g) was added 10% palladium carbon (containing 50% water, 7.2 g) and the mixture was stirred for 4 hours at room temperature. The catalyst was filtered off over celite (registered trademark) and the filtrate was concentrated. The residue was recrystallized from ethyl acetate-heptane (1:2) to give the compound of the present invention (19.3 g) having the following physical data.

TLC: 0.25 (chloroform:methanol=10:1);

NMR (CD₃OD): δ 7.24-7.20 (m, 2H), 7.14-7.08 (m, 1H), 6.71 (t, J=74.8 Hz, 1H), 5.00-4.90 (m, 1H), 3.70-3.57 (m, 2H), 3.45-3.34 (m, 2H), 2.50-2.30 (m, 4H), 2.10-1.60 (m, 8H).

REFERENCE EXAMPLE 11

2-(4-(3-cyclopentyloxy-4-difluoromethoxyphenyl)-4-cyanopiperidin-1-yl)acetic Acid Ethyl Ester

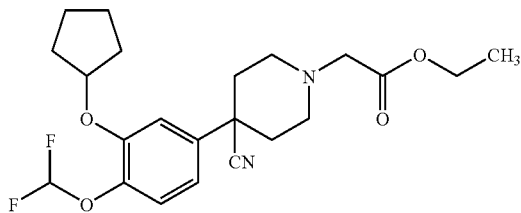

To a solution of the compound prepared in example 1 (19.8 g) in N,N-dimethylformamide (53 ml) were added potassium carbonate (18.4 g) and ethyl bromoacetate (5.89 ml) and the mixture was stirred for 1.5 hours at 50° C. To the reaction mixture was added water (160 ml) and it was extracted by tert-butyl methyl ether (160 ml). The organic layer was washed by water (80 ml×2) and concentrated to give the title compound (23.4 g) having the following physical data.

TLC: 0.47 (hexane:ethyl acetate=1:1);

NMR (CDCl₃): δ 7.18-7.00 (m, 3H), 6.54 (t, J=75.0 Hz, 1H), 4.85-4.78 (m, 1H), 4.22 (q, J=7.0 Hz, 2H), 3.31 (s, 2H), 3.10 (brd, J=11.8 Hz, 4H), 2.68 (td, J=11.8, 3.2 Hz, 4H), 2.30-2.20 (m, 4H), 2.20-1.60 (m, 8H), 1.30 (t, J=7.0 Hz, 3H).

EXAMPLE 2

2-(4-(3-cyclopentyloxy-4-difluoromethoxyphenyl)-4-cyanopiperidin-1-yl)acetic Acid Monohydrate

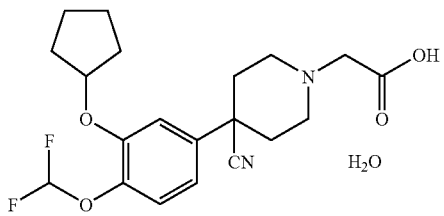

To a solution of the compound prepared in reference example 9 (17.7 g) in methanol (200 ml) was added 1N aqueous solution of sodium hydroxide (86.6 ml) and the mixture was stirred for 2 hours at room temperature. Under cooling with ice to the reaction mixture was added 2N hydrochloric acid (43 ml). The precipitate was collected and washed by 2N methanol-water (1:2) (150 ml) and diethyl ether to give a crude compound (13.36 g). The crude compound (12.44 g) was recrystallized from ethanol (144 ml)-water (96 ml) and dried under reduced pressure (3 mmHg) for 12 hours at 25° C. to give the compound of the present invention (monohydrate) (11.49 g) having the following physical data.

TLC: 0.48 (chloroform:methanol=8:2);

NMR (DMSO-d₆): δ 7.22-7.19 (m, 2H), 7.09 (dd, J=8.7, 2.1 Hz, 1H), 7.00 (t, J=74.4 Hz, 1H), 5.01-4.92 (m, 1H), 4.00-2.60 (br, 1H), 3.24 (s, 2H), 3.04-2.95 (m, 2H), 2.70-2.50 (m, 2H), 2.16-1.80 (m, 6H), 1.80-1.50 (in, 6H).

EXAMPLE 2(1)

2-(4-(3-cyclopentyloxy-4-difluoromethoxyphenyl)-4-cyanopiperidin-1-yl)acetic Acid Monohydrate

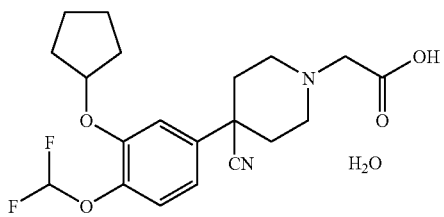

By the same procedure as described in example 2 using the compound prepared in reference example 11 in place of the compound prepared in reference example 9, the compound of the present invention having the following physical data was given.

TLC: 0.48 (chloroform:methanol=8:2);

NMR (DMSO-d₆): δ 7.25-7.16 (m, 2H), 7.09 (dd, J=8.4, 2.2 Hz, 1H), 7.00 (t, J=74.4 Hz, 1H), 5.08-4.92 (m, 1H), 3.24 (s, 2H), 3.12-2.94 (m, 2H), 2.70-2.46 (m, 2H), 2.20-1.43 (m, 12H).

EXAMPLE 3

2-(4-(3-cyclopentyloxy-4-difluoromethoxyphenyl)-4-cyanopiperidin-1-yl)acetic Acid Pentahydrate

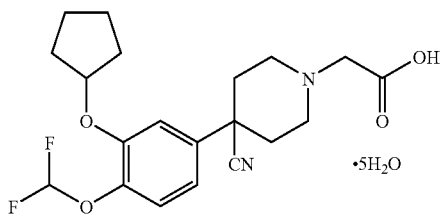

To a solution of the compound prepared in reference example 11 (30.7 g) in ethanol (146 ml) was added 2N aqueous solution of sodium hydroxide (43.8 ml) at room temperature and the mixture was stirred for 2 hours at room temperature. The reaction mixture was neutralized by adding 2N hydrochloric acid (43.8 ml) and the mixture was concentrated to give a solid (34.82 g). Part (5.0 g) of the solid was recrystallized from ethanol-water (2:1) to give the compound of the present invention (pentahydrate) (4.41 g) having the following physical data.

TLC: 0.48 (chloroform:methanol=8:2).

EXAMPLE 4

2-(4-(3-cyclopentyloxy-4-difluoromethoxyphenyl)-4-cyanopiperidin-1-yl)acetic Acid Monohydrate

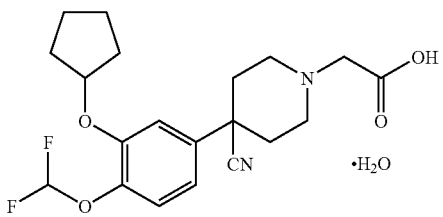

The compound prepared in example 3 (4.41 g) was dried under reduced pressure (3 mmHg) to give the compound of the present invention (monohydrate) (3.73 g) having the following physical data.

TLC: 0.48 (chloroform:methanol=8:2);

NMR (DMSO-$d_6$): δ 7.22-7.19 (m, 2H), 7.09 (dd, J=8.7, 2.1 Hz, 1H), 7.00 (t, J=74.4 Hz, 1H), 5.01-4.92 (m, 1H), 4.00-2.60 (br, 1H), 3.24 (s, 2H), 3.04-2.95 (m, 2H), 2.70-2.50 (m, 2H), 2.16-1.80 (m, 6H), 1.80-1.50 (m, 6H).

COMPARISON EXAMPLE 1

2-(4-(3-cyclopentykoxy-4-difluoromethoxyphenyl)-4-cyanopiperidin-1-yl)acetic Acid

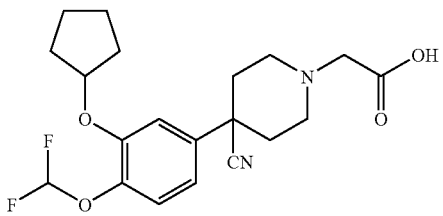

A mixture of the compound prepared in reference example 11 (185 mg), ethanol (3 ml) and 2N aqueous solution of sodium hydroxide (0.44 ml) was stirred for 1.5 hours at room temperature. The reaction mixture was neutralized with 2N hydrochloric acid (0.44 ml) and azeotroped with toluene. The residue was purified by column chromatography on silica gel (chloroform:methanol: water=10:2:0.1) to give the compound of the present invention (176 mg) having the following physical data.

TLC: Rf 0.35 (chloroform:methanol: acetic acid=10:1: 0.2);

NMR (CDCl$_3$): δ 7.25-7.15 (m, 2H), 7.09 (dd, J=8.1, 2.1 Hz, 1H), 7.01 (t, J=75.0 Hz, 1H), 4.98 (m, 1H), 3.60-3.00 (br, 1H), 3.26 (s, 2H), 3.10-2.95 (m, 2H), 2.70-2.50 (m, 2H), 2.20-2.00 (m, 4H), 2.00-1.80 (m, 2H), 1.80-1.60 (m, 4H), 1.65-1.50 (m, 2H).

FORMULATION EXAMPLE 1

The following components were admixed in a conventional method and punched out to obtain 100 tablets each containing 50 mg of the active ingredient.

| | |
|---|---|
| 2-(4-(3-cyclopentyloxy-4-difluoromethoxyphenyl)-4-cyanopiperidin-1-yl)acetic acid monohydrate | 5.0 g |
| Carboxymethyl cellulose calcium (disintegrating agent) | 0.2 g |
| Magnesium stearate (lubricant) | 0.1 g |
| Microcrystalline cellulose | 4.7 g |

FORMULATION EXAMPLE 2

The following components were admixed in a conventional method, and the solution was sterilized in a conventional method, placed at 5 ml into ampoules and freeze-dried in a conventional method to thereby obtain 100 ampoules each containing 20 mg of the active ingredient.

| | |
|---|---|
| 2-(4-(3-cyclopentyloxy-4-difluoromethoxyphenyl)-4-cyanopiperidin-1-yl)acetic acid monohydrate | 2.0 g |
| Mannitol | 20 g |
| Distilled water | 1000 ml |

The invention claimed is:

1. A piperidine derivative of formula (I):

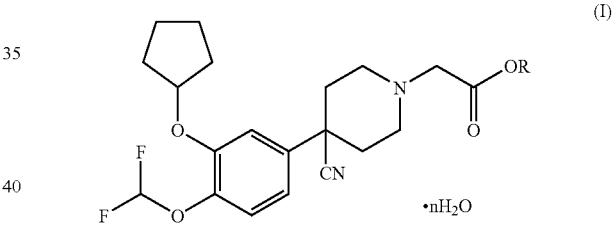

(I)

wherein R is hydrogen, and n is an integer of 1 or 5.

2. The compound according to claim 1, which is 2-(4-(3-cyclopentyloxy-4-difluoromethoxyphenyl)-4-cyanopiperidin-1-yl)acetic acid monohydrate.

3. A composition for the treatment of asthma, chronic obstacle pulmonary disease, allergic rhinitis, atopic dermatitis, allergic conjunctivitis or seasonal conjunctivitis, which comprises the compound according to claim 1 in an effective amount and pharmaceutical carriers.

4. A method for the treatment of asthma, chronic obstacle pulmonary disease, allergic rhinitis, atopic dermatitis, allergic conjunctivitis or seasonal conjunctivitis, which comprises administering a therapeutically effective amount of a compound according to claim 1.

* * * * *